United States Patent
Zapata et al.

(10) Patent No.: US 7,388,195 B2
(45) Date of Patent: Jun. 17, 2008

(54) APPARATUS AND SYSTEMS FOR PROCESSING SAMPLES FOR ANALYSIS VIA ION MOBILITY SPECTROMETRY

(75) Inventors: Angela M. Zapata, Arlington, MA (US); Ernest S. Kim, Cambridge, MA (US); Priya Agrawal, Los Angeles, CA (US); Melissa D. Krebs, Quincy, MA (US); Cristina E. Davis, Berkeley, CA (US)

(73) Assignee: Charles Stark Draper Laboratory, Inc., Cambridge, MA (US)

( * ) Notice: Subject to any disclaimer, the term of this patent is extended or adjusted under 35 U.S.C. 154(b) by 153 days.

(21) Appl. No.: 11/241,747

(22) Filed: Sep. 30, 2005

(65) Prior Publication Data

US 2006/0163471 A1    Jul. 27, 2006

Related U.S. Application Data

(60) Provisional application No. 60/695,502, filed on Jun. 30, 2005, provisional application No. 60/615,571, filed on Sep. 30, 2004.

(51) Int. Cl.
*B01D 59/44* (2006.01)
*H01J 49/00* (2006.01)

(52) U.S. Cl. .................. 250/288; 250/282; 250/426; 250/293; 250/287; 250/286; 250/281; 250/283; 250/324; 250/423 R; 250/290; 250/292; 324/464; 331/126; 386/46; 386/125

(58) Field of Classification Search ................ 250/282, 250/426, 288, 293, 287, 286, 281, 283, 324, 250/423 R, 290, 292; 324/464; 331/126; 386/46, 125

See application file for complete search history.

(56) References Cited

U.S. PATENT DOCUMENTS 7,057,168 B2 *   6/2006   Miller et al. ............... 250/287
7,129,482 B2 *  10/2006   Miller et al. ............... 250/288
7,241,989 B2 *   7/2007   Miller et al. ............... 250/282

* cited by examiner

*Primary Examiner*—Jack I. Berman
*Assistant Examiner*—Meenakshi S Sahu
(74) *Attorney, Agent, or Firm*—Goodwin Procter LLP

(57) ABSTRACT

The invention provides an interface assembly for delivering an ionized analyte from an ionization apparatus into an ion mobility spectrometer. This allows analysis of biological and non-biological samples, even non-volatile solids, via differential mobility spectrometry, without fragmentation of molecules. The invention also provides portable sample analysis systems that operate at ambient pressure. Systems of the invention may be used for high molecular weight species detection, for example, drinking water contaminants, pathogenic biological agents, bio-organic substances, non-biological material, peptides, proteins, oligonucleotides, polymers, bacteria, and hydrocarbons.

26 Claims, 21 Drawing Sheets

APPARATUS AND SYSTEMS FOR PROCESSING SAMPLES FOR ANALYSIS VIA ION MOBILITY SPECTROMETRY

PRIOR APPLICATIONS

The present application claims the benefit of U.S. Provisional Patent Application No. 60/615,571 filed Sep. 30, 2004, and U.S. Provisional Patent Application No. 60/695,502 filed Jun. 30, 2005, which are hereby incorporated by reference in their entirety.

FIELD OF THE INVENTION

This invention relates generally to systems for processing samples for analysis via ion mobility spectrometry. More particularly, the invention relates to an interface assembly for delivering an ionized analyte from an ionization apparatus into an ion mobility spectrometer, for example, a field asymmetric ion mobility spectrometer (FAIMS).

BACKGROUND OF THE INVENTION

The ability to detect and identify explosives, drugs, and chemical and biological agents, as well as the ability to monitor air and water quality, has become increasingly more important given increasing terrorist and military activities and environmental concerns. Spectrometry is a powerful analytical tool for identifying molecular components of these substances. Certain known methods for detection and/or quantification of the concentration of such components include conventional mass spectrometers, time-of-flight ion mobility spectrometers, as well as field asymmetric ion mobility spectrometers (FAIMS).

Mass spectrometers identify molecular components according to their characteristic "weight" or mass-to-charge ratio. Typically, a mass spectrometer-based analytical system includes the following components: a device for introducing the sample to be analyzed, such as a liquid or gas chromatograph, direct insertion probe, syringe pump, or autosampler; an ionization source for producing ions from the analyte (as referred to herein, an analyte is the sample itself or one or more components of the sample); an analyzer for separating the ions according to their mass-to-charge ratio; a detector for measuring the abundance of the ions; and a data processing system that produces a mass spectrum of the analyte.

Mass spectrometers are very sensitive, highly selective, and provide a fast response time. Mass spectrometers, however, are large, expensive, and require significant amounts of power to operate. They also often require several different types of pumps to maintain a vacuum-pressure in the analyzer region of about $10^{-6}$ Torr in order to isolate the ions from neutral molecules and to permit detection of the selected ions.

Another, less complex spectrometric technique is time-of-flight (TOF) ion mobility spectrometry, currently implemented in most portable chemical weapons and explosives detectors. TOF spectrometry is not based solely on mass, but is also based on charge and cross-section of the molecule. While conventional TOF devices are relatively inexpensive, they suffer from several limitations. First, molecular species identification via TOF spectrometry is not as conclusive and accurate as via mass spectrometry. Time-of-flight ion mobility spectrometers typically have unacceptable resolution and sensitivity limitations. The sample volume through the detector of a TOF spectrometer is small, so in order to increase spectrometer sensitivity, either expensive electronics are required to provide extremely high sensitivity, or a concentrator is required, adding to system complexity and cost. In addition, a gate and gating electronics are usually needed to control the injection of ions into the drift tube. Miniaturization, or micromachining, of TOF spectrometers worsens sensitivity. For example, problems occur when the drift tube length of a TOF spectrometer is less than about 2 inches. In time-of-flight ion mobility, the resolution is typically proportional to the length of the drift tube. The longer the tube, the better the resolution, provided that the drift tube is also wide enough to prevent ions from being lost to the side walls due to diffusion. Thus, fundamentally, miniaturization of TOF ion mobility systems leads to a degradation in system performance.

Yet another technique, field asymmetric ion mobility (FAIM) spectrometry, allows a selected ion to pass through a filter while blocking the passage of undesirable ions. Conventional FAIM spectrometers are large and expensive; for example, current devices are nearly a cubic foot in size and cost over $25,000. These systems are not suitable for use in applications requiring small detectors. They are also relatively slow, taking as much as one minute to produce a complete spectrum of the sample gas, they are difficult to manufacture, and they are poorly suited for mass production. Moreover, the pumps that are required to draw a sample medium into the spectrometer and to provide a carrier gas can be rather large and consume large amounts of power.

Recently, microDMx™ sensor chip technology, an improvement over conventional FAIM spectrometry, has been developed by The Charles Stark Draper Laboratory (Cambridge, Mass.) ("Draper Laboratory") and is presently available from Sionex Corporation (Waltham, Mass.) ("Sionex"). This sensor chip technology, as described in, for example, U.S. Pat. Nos. 6,495,823 and 6,512,224, which are both incorporated herein by reference, demonstrates that extremely small, accurate, and fast FAIM filter and detection systems can be implemented using MEMS and microfabrication technology to define a flow path between a sample inlet and an outlet using a pair of spaced substrates and disposing an ion filter within the flow path. The filter includes a pair of spaced electrodes, with one electrode associated with each substrate, and a controller for selectively applying a bias voltage and an asymmetric periodic voltage across the electrodes to control the path of ions through the filter. In its various aspects, this technology separates and detects ionized compounds based on their differential mobilities through the sensor chip described above. Ionized compounds have mobilities, which are a function of their charge, mass, and cross-sectional area. By applying an RF and DC field to the sensor chip it can act as a filter selecting a chosen ion or collection of ions. The applied DC and RF fields can be used as parameters to identify the ions together with additional information, such as field dependence. This differential mobility spectrometer device ("DMS") is small, inexpensive, highly sensitive to the parts-per-trillion range and is capable of detecting a variety of chemicals and biological materials.

One obstacle to utilizing this technology to its full potential, however, is the methodologies currently used to ionize and introduce the samples into the DMS for analysis. Current methods of introducing samples into the DMS include the following: headspace sampling, pyrolysis, gas sampling, and conventional gas spectrometry (i.e. volatilizing and separating samples using a Gas Chromatography (GC) column). Each of these current methods have drawbacks.

In headspace sampling, gaseous volatiles in the headspace above liquid samples are directed through a Gas Chromatography (GC) column to separate components in the sample, which are then introduced into the DMS. Alternatively, the gas volatiles may be introduced directly into the DMS for analysis. This method is limited to analysis of volatiles in the headspace above liquid samples. Semi-volatile and non-volatile components, however, are difficult to examine with this sample introduction technique because of their low vapor pressure and resulting low concentration in the headspace above the liquid sample.

Pyrolysis involves breaking-apart chemical bonds using thermal energy. The resulting molecular fragments are often ion species. Both solid and liquid samples can be pyrolyzed. The resulting gas is directed through a GC column, then introduced into the DMS. Alternatively, the pyrolyzed material may be introduced directly into the DMS for analysis. Pyrolysis, however, is destructive of large molecular weight samples, and, as such, this technique often results in excessive fragmentation of the molecules. It may be impossible to detect certain higher molecular weight compounds using this technique.

In gas sampling, gaseous samples are introduced directly into the DMS, or are passed through a GC column, then introduced in to the DMS. This method is limited to examination of gaseous samples.

For certain volatile and semi-volatile liquid organic compounds, samples can be volatilized and separated using the GC column, and then transported into the DMS. Again, this is not possible for analysis of non-volatile substances, or for certain semi-volatile substances.

Current methods of ionizing samples for analysis in the DMS include the use of the following: UV-photoionization lamp, radioactive $^{63}$Ni and $^{241}$Am sources, and plasma corona discharge devices.

A UV-photoionization lamp may only be used to ionize substances with ionization potentials up to 11.7 eV, making such methods suitable for processing certain volatile and semi-volatile compounds, but not non-volatile liquids. Also, the surface of the bulb often becomes coated with residues from sample introduction, reducing ionization efficiency.

Radioactive $^{63}$Ni and $^{241}$Am sources provide ionization energy of up to 67 keV and 59.5 keV, respectively. Radioactive sources must be registered with government and institutional safety offices. Special handling licenses are required. These requirements restrict the widespread use of these ionization sources in non-R&D devices, keeping them from being truly mobile or field-deployable.

Thus, limitations of conventional methods of sample preparation for spectral analysis using a differential mobility spectrometer (DMS) impede exploitation of this potentially versatile device, particularly for analysis of bio-organic molecules, microorganisms, and other biological compounds, as well as high molecular weight non-biological compounds such as polymers and hydrocarbons. Specifically, there is a need for systems and methods for ionizing and converting non-volatile and/or semi-volatile biological and other macromolecular analytes into the gas phase for analysis in a DMS, i.e. a FAIMS, preferably without fragmentation of the molecules. There is also a need for portable analysis systems with micromachined components, as well as systems that do not require operation under high vacuum.

SUMMARY OF THE INVENTION

The invention combines recent advances in ion mobility spectrometers with newly-developed ionization processes to furnish portable sample analysis systems that operate under ambient pressure and that are suitable for analysis of high molecular weight bio-organic and non-biological substances. These systems are made possible by an interface assembly that delivers an ionized analyte from an ionization apparatus into an ion mobility spectrometer, for example, a DMS or FAIMS. Solid, liquid, gas, and plasma samples may be analyzed.

The interface assembly allows use of advanced ionization techniques—such as ambient pressure matrix-assisted laser desorption ionization (AP-MALDI) and/or electrospray ionization (ESI), which are miniaturizable, portable, and may operate at ambient pressure—together with differential ionization spectrometers, which are also miniaturizable, portable, and may operate at ambient pressure. The interface assembly further offers interchangeability between different types of ionization apparatus for use with a differential mobility spectrometer.

Analysis of biological and non-biological molecules of high molecular weight, or example, over 500 Da, is made possible by systems of the invention. Analysis of biological analytes by DMS poses at least two challenges: first, biological analytes are generally non-volatile molecules in liquid matrices, and are therefore difficult to convert into a gas phase for introduction into the DMS. Second, typical vaporization/ionization methods compromise the chemical integrity of the bio-molecule, increasing the complexity of the DMS spectra generated and reducing its utility. In certain embodiments, the technology disclosed herein overcomes these challenges by using its interface assembly to combine either of two methods along with DMS-Electrospray Ionization (ESI), in which a sample is transformed into an expanding gas jet experiencing a large electric field, and AP-MALDI, which is used to generate ionized gases from solid and dried liquid samples. Alternatively, other laser-based ionization methods may be used, for example, surface assisted ionization in which modification of specialized surfaces impart charge to molecules of interest, as well as micromachined device- or surface-assisted ionization in which charge is imparted onto analytes via laser excitation.

There are several characteristics of AP-MALDI and ESI which make them desirable methods of sample introduction to a DMS. One of these characteristics is the "softness" of the ionization process. In the case of ESI, the gentle ionization allows both the preservation of non-covalent interactions between molecules in the gas phase that existed in solution, and the study of three-dimensional conformations. In AP-MALDI, the ionization is again very gentle and can desorb and ionize large molecules while keeping them intact. AP-MALDI is often used to prepare proteins, peptides, and other large biological macromolecules for mass spectrometry analysis.

In one aspect, the invention provides an interface assembly for delivering an ionized analyte from an ionization apparatus into an ion mobility spectrometer, the interface assembly including: a capillary tube through which the ionized analyte flow; an ion flow generator that draws the ionized analyte from the ionization apparatus into the interface assembly and through the capillary tube; and a gas manifold assembly through which a carrier gas flows, the gas manifold assembly disposed in relation to the capillary tube to allow infusion of the ionized analyte into the carrier gas and delivery of the resulting gas stream into the ion mobility spectrometer.

In one embodiment, the ion flow generator includes a high voltage assembly that draws the ionized analyte into the interface assembly using a high voltage. The voltage assembly may operate, for example, with a potential of up to about 5000 V, with a potential of about 1000 V or more, with a potential between about 1000V and about 5000 V. The voltage assembly may also operate with a potential above 5000 V or below 1000V. In one embodiment, the high voltage assembly includes an electrode plate at a highly negative voltage, for example, a voltage below about −1000 V, below about −2000 V, below about −3000 V, or below about −4000V. In one embodiment, the high voltage assembly includes an outer electrode and an inner electrode that operate at different voltages.

In one embodiment, the ion flow generator of the interface assembly includes: an electrical component for drawing the ionized analyte from the ionization apparatus into the interface assembly using an electrical field; a mechanical component for drawing the ionized analyte from the ionization apparatus into the interface assembly using a pressure differential; or both.

In certain embodiments, at least a portion of the gas manifold assembly is disposed about the capillary tube, thereby allowing infusion of the ionized analyte into the carrier gas.

The ion flow generator of the interface assembly may draw a sample gas from the ionization apparatus, where the sample gas contains (or is) the ionized analyte. The sample gas may further include ionized matrix molecules, ionized solvent, or both. The sample gas may include non-ionized species as well. In certain embodiments, non-analyte molecules are filtered from the sample gas in the interface assembly. Furthermore, in certain embodiments, the interface assembly includes an orifice through which a break-up gas flows for dissolution of the sample gas. The break-up gas may be heated and may contain air or nitrogen.

In one embodiment, the carrier gas of the interface assembly contains nitrogen. In certain embodiments, the carrier gas contains argon, helium, air, oxygen, and/or carbon dioxide. In certain embodiments of the interface assembly, the ionization apparatus and/or the ion mobility spectrometer operate at about ambient pressure.

In certain embodiments, the ionization apparatus may be an ambient pressure matrix-assisted laser desorption ionization (AP-MALDI) apparatus or an electrospray ionization apparatus. In certain embodiments, the ion mobility spectrometer is a field asymmetric ion mobility spectrometer.

In certain embodiments, the interface apparatus further includes a mount block with a mechanism for detachably connecting the interface assembly to the ionization apparatus. The mechanism may be a hinge-and-latch mechanism, for example. The mechanism may allow interchange between two or more machines that serve as the ionization apparatus. This may provide additional versatility. In one embodiment, the mechanism allows interchange between an ambient pressure matrix-assisted laser desorption ionization apparatus and an electrospray ionization apparatus as the ionization apparatus of the interface apparatus.

In another aspect, the invention provides a system for delivering an analyte into an ion mobility spectrometer, the system include an ionization apparatus with a laser for providing energy to ionize the analyte, as well as an interface assembly for receiving the ionized analyte and infusing the ionized analyte into a carrier gas stream for transport into an ion mobility spectrometer. In certain embodiments, the ion mobility spectrometer is a FAIMS. The ionization apparatus may include an ionization chamber and a support within the ionization chamber, upon which is located a solid containing the analyte in an ionization-assisting matrix, wherein the laser provides energy to desorb and ionize the analyte in the presence of the ionization-assisting matrix. The support may be a target plate. The sample containing the analyte may be dissolved in a solution, the solution including a solvent and a compound that absorbs ultraviolet light. The solution may be placed on the support and solvent may be evaporated from the solution, leaving the solid, which contains the analyte in the ionization-assisting matrix. In one embodiment, the sample is a solid, and in another embodiment, the sample is a liquid. The sample may also be a gas or plasma.

In one embodiment of the system for delivering an analyte into an ion mobility spectrometer, the analyte has a molecular weight, for example, above about 500 Da, above about 1000 Da, above about 5000 Da, above about 10,000 Da, above about 20,000 Da, above about 25,000 Da, above about 30,000 Da, above about 40,000 Da, above about 50,000 Da, or above about 60,000 Da. In one embodiment, the carrier gas contains air or nitrogen. In one embodiment, the ionization apparatus performs liquid matrix assisted laser desorption ionization, surface assisted ionization, micromachined surface or device assisted ionization, or any combination thereof.

It is contemplated that the invention includes methods of detecting the analyte using the systems described herein.

In yet another aspect, the invention provides a system for sample analysis including: an ionization source for producing ionized analyte from the sample, the ionization source including an ambient pressure matrix-assisted laser desorption ionization apparatus, an electrospray ionization apparatus, or both; a field asymmetric ion mobility spectrometer for receiving and detecting the ionized analyte; and an interface assembly for delivering the ionized analyte from the ionization source to the field asymmetric ion mobility spectrometer. The ionization source may be an ambient pressure matrix-assisted laser desorption ionization apparatus.

In certain embodiments of the system for sample analysis, the ionization source includes: an ionization chamber; a support within the ionization chamber, upon which is located a solid comprising the analyte in an ionization-assisting matrix; and a laser for providing energy to desorb and ionize the analyte in the presence of the ionization-assisting matrix. The laser may be a nitrogen laser, a $CO_2$ laser, a Er-YAG laser, a Nd-YAG laser, a Er-YILF laser, or a Er-YSGG laser. One or more lasers may be part of the ionization source. The energy of the laser may be from about $10^6$ to about $10^8$ W/cm$^2$. The laser may produce light at a wavelength between about 200 and about 600 nm or between about 1.4 and about 12 μm.

In certain embodiments, the system for sample analysis further includes the field asymmetric ion mobility spectrometer to which the interface assembly delivers the ionized analyte. The system may be portable and/or may operate at ambient pressure.

Samples that may be analyzed using systems and/or methods of the invention include liquids, solids, gases, and plasmas. The sample may be or contain drinking water, a pathogenic biological agent, a non-biological material, a bio-organic substance, human tissue, animal tissue, a skin emanation, a peptide, a protein, an oligonucleotide, an oligosaccharide, DNA, RNA, bacteria, a polymer, a hydrocarbon, a VOC, breath, blood, urine, plasma, and extracts, concentrates, fragments, and/or combinations thereof. The analyte may have a molecular weight, for example, above about 500 Da, above about 1000 Da, above about 5000 Da, above about 10,000 Da, above about 20,000 Da, above about 25,000 Da, above about 30,000 Da, above about 40,000 Da, above about 50,000 Da, or above about 60,000 Da. The analyte may have a molecular weight up to about 100,000 Da. This molecular weight may be a number-average or weight-average molecular weight, for example.

The invention also provides a computer apparatus that includes a memory that stores code defining a set of instructions, and a processor that executes the instructions to perform one or more methods of the invention described herein.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

FIG. 20A shows data obtained when the AP-MALDI laser is off, FIG. 20B shows data obtained when the AP-MALDI laser is fired on a blank target plate, and FIG. 20C shows data obtained when the AP-MALDI laser is fired on a sample of α-cyano-2-hydroxycinnamic acid, according to an illustrative embodiment of the invention.

DETAILED DESCRIPTION

Figure 1:
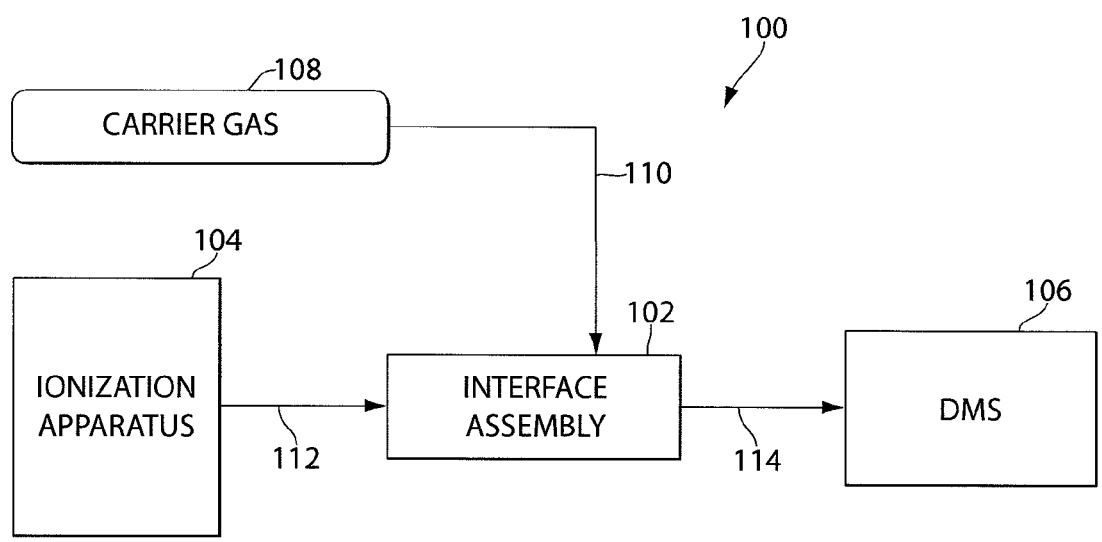
FIG. 1 is a block diagram representing a system for spectroscopic analysis of a sample, the system including an interface assembly for delivering ionized sample from an ionization apparatus into an ion mobility spectrometer according to an illustrative embodiment of the invention.

A mechanical interface assembly is presented that allows introduction of high molecular weight biological and non-biological samples into a differential mobility spectrometer (DMS) using electrospray ionization (ESI) or ambient pressure matrix-assisted laser desorption ionization (AP- MALDI) sample preparation approaches. In one embodiment, the interface assembly draws sample ions in from either an AP-MALDI or ESI needle with an electrode plate held at a high negative voltage (for example, from about −1000 V to about −3000 V), dissolves the sample into fine particles by using an optionally-heated break-up gas flow over the ESI or AP-MALDI sample plume, combines the sample ion flow with a hot nitrogen carrier gas flow to transport the sample ions into the DMS detector, matches the optimum instrument conditions of both introduction methods to those of the DMS sensor, and facilitates a fast connection and interchange of either the ESI or AP-MALDI units to the DMS sensor. The interface assembly preferably uses both a carrier gas and a break-up gas, where the break-up gas aids in dissolution of the sample gas from the ionization source and filters out unwanted molecules/ions, thereby improving resolution.

MicroDMx™ sensor chip technology, as used in a DMS apparatus, is described in U.S. Pat. Nos. 6,495,823 and 6,512,224, which are both incorporated herein by reference in their entirety. Extremely small, accurate and fast Field Asymmetric Ion Mobility filter and detection systems can be implemented using MEMS and microfabrication technology to define a flow path between a sample inlet and an outlet using a pair of spaced substrates and disposing an ion filter within the flow path. The filter includes a pair of spaced electrodes, with one electrode associated with each substrate, and a controller for selectively applying a bias voltage and an asymmetric periodic voltage across the electrodes to control the path of ions through the filter. In its various aspects, this technology separates and detects ionized compounds based on their differential mobilities through the sensor chip described above. Ionized compounds have mobilities, which are a function of their charge, mass and cross-sectional area. By applying an RF and DC field to the sensor chip it can act as a filter selecting a chosen ion or collection of ions. The applied DC and RF fields can be used as parameters to identify the ions together with additional information, such as field dependence. Analysis of biological and high molecular weight non-biological molecules by DMS poses difficulties because such analytes are generally non-volatile molecules and are therefore difficult to convert into a gas phase for introduction into the DMS. Furthermore, typical vaporization/ionization methods compromise the chemical integrity of the molecule, increasing the complexity of the DMS spectra generated and reducing its utility.

In certain embodiments, the technology disclosed herein overcomes these challenges by using its interface assembly to combine either (or both) of two ionization methods along with DMS-Electrospray Ionization (ESI), in which a sample is transformed into an expanding gas jet experiencing a large electric field, and AP-MALDI, which is used to generate ionized gases from solid and dried liquid samples. In one embodiment of ESI, the sample is introduced at flow rates less than 1 ml/min into a pneumatic nebulizer needle. Pneumatic nebulization occurs due to the force with which the sample is forced to exit a small orifice by a gas at flow rates in the order of 1 LPM. As the gas expands small, charged liquid droplets break down until a plume of fine particles is created.

The second method is AP-MALDI, mentioned above, which has been used to generate ionized gases from solid and dried liquid samples. As described in more detail in, for example, U.S. Pat. No. 6,849,847, incorporated herein by reference, in AP-MALDI, the sample is dispersed into a matrix containing a compound which, when exposed to an ultraviolet laser source, absorbs and transfers some energy to the sample, which, in turn, causes the sample to desorb from the plate and get ionized at atmospheric pressure.

According to MALDI, the analyte is mixed in a solvent containing small organic molecules having a strong absorption at a particular optical wavelength (hereinafter referred to as the "matrix"). The solution containing the dissolved analyte and matrix is applied to a metal probe tip or target substrate. As the solvent evaporates, the analyte and matrix co-precipitate out of solution to form an analyte-matrix crystal on the target substrate. The co-precipitate is then irradiated with a short laser pulse inducing the accumulation of a large amount of energy in the co-precipitate through electronic excitation or molecular vibration of the matrix molecules. The matrix dissipates the energy by desorption, carrying along the analyte into the gaseous phase. During this desorption process, charge transfer between the photo-excited matrix and the analyte forms analyte ions.

Conventionally, the MALDI technique is performed using a time-of-flight analyzer, although other mass analyzers, such as an ion trap, an ion cyclotron resonance mass spectrometer, and quadrupole time-of-flight, are also used. These analyzers, however, must operate under high vacuum, e.g., less than $1 \times 10^{-5}$ Torr, which, among other disadvantages, may limit sample throughput and make testing samples more difficult and expensive to perform.

To overcome these disadvantages, a technique often referred to as atmospheric pressure matrix-assisted laser desorption ionization ("AP-MALDI") has been recently developed, employing the MALDI technique at atmospheric pressure. The MALDI and the AP-MALDI approaches have much in, common, e.g., both techniques are based on the process of pulsed laser beam desorption/ionization of a solid-state target material resulting in production of gas phase analyte molecular ions. The AP-MALDI technique, however, does not require the ionization process to occur in a vacuum, resulting in a number of performance and cost advantages. For example, the AP-MALDI process is very gentle and can desorb and ionize large molecules (AP-MALDI test standards range from 1-20 kDa) while keeping them intact. For this reason, AP-MALDI may be used to analyze proteins, peptides, and other large biological macromolecules. AP-MALDI, however, has not heretofore been adapted for preparing samples for DMS analysis.

Potential applications of the DMS technology supplemented by AP-MALDI or ESI technique for sample ionization ("AP-MALDI-DMS" and "ESI-DMS", respectively) include analyses of proteins, peptides, bacteria, organisms, and other biological macromolecules, as well as non-biological polymers, both in research and industrial settings. As mentioned above, one of many benefits of this technique is its ability to desorb and ionize large molecules without destroying or fracturing them. The AP-MALDI-DMS system may be used, for example, in the following applications: testing the purity of synthesized biological molecules; testing the purity of synthesized non-biological molecules; protein identification and proteomics research; rapid analysis of low-molecular-weight polymers, proteolytically digested proteins and samples derived from proteins; analysis of plasticizers and low-molecular weight polymers; identification and characterization of polymers and their impurities; field-portable detection system for chemical and biological weapons agents; probes for space- and interplanetary craft for on-site chemical testing and screening for biological evidence; detection of pathogens in food and water supplies; analysis of pharmaceutical compounds in intact tissue samples; and rapid emergency/operating table diagnosis of biological samples.

Throughout the description, where systems and methods are described as having, including, or comprising specific steps, it is contemplated that, additionally, there are systems and methods of the present invention that consist essentially of, or consist of, the recited steps.

It should be understood that the order of steps or order for performing certain actions is immaterial so long as the invention remains operable. Moreover, two or more steps or actions may be conducted simultaneously. It should also be understood that steps, apparatus elements, or system elements that are described with respect to one embodiment may also be used with respect to other embodiments described herein.

Where the use of a specific material is described, it is also contemplated that suitable alternative materials may be used with respect to the embodiments described herein.

The mention herein of any system, method, protocol, or publication, for example, in the Background section, is not an admission that the system, method, protocol, or publication serves as prior art with respect to any of the claims presented herein.

FIG. 1 is a block diagram 100 representing a system for spectroscopic analysis of a sample, the system including an interface assembly 102 for delivering ionized sample from an ionization apparatus 104 into an ion mobility spectrometer, i.e. a differential mobility spectrometer (DMS) 106. The carrier gas 108, for example, nitrogen or air, flows through a conduit 110 into the interface assembly 102. In various embodiments, the analysis system is an AP-MALDI-DMS system that includes the AP-MALDI as the ionization apparatus 104, the AP-MALDI-DMS interface assembly 102, the carrier gas supply 108, and the DMS 106. In general overview, the sample gas is produced in the AP-MALDI unit and is transported to the AP-MALDI-DMS interface assembly, where it is infused into the flow of a carrier gas, such as, for example, nitrogen. The sample and carrier gas then flow through the DMS unit where the sample is analyzed.

In other embodiments, the analysis system is an ESI-DMS system, and the components for ESI-DMS are similar as for the AP-MALDI system, with the exception of the ESI nebulizer replacing the AP-MALDI unit. Specifically, the main sample handling components of the ESI-DMS system are the ESI nebulizer as the ionization apparatus 104, the interface assembly 102, the carrier gas supply 108, and the DMS 106. For ESI operation, the sample is aerosolized, i.e. converted into a gaseous suspension of fine liquid particles, and ionized in the ESI nebulizer. A commercially available, high-precision syringe pump (for example, Pump 11 Pico Plus, Harvard Apparatus) is used to deliver sample to the electrospray nebulizer needle assembly (available from, for example, Agilent Technologies, Palo Alto, Calif.).

In one embodiment, a nitrogen gas flow, at a typical rate of about 1 LPM enters the nebulizer needle in a flow path concentric to the sample flow. As the gas-sample mixture exits the nebulizer needle through, for example, a 800 μm orifice, the expanding jet fractionates the emerging liquid producing the fine sample aerosol. The gas jet produced by the ESI unit, is exposed to a voltage potential, developed between the end of the needle and the High Voltage Assembly on the interface module, on the order of −1 to −4 kV maintained by a high voltage power supply (Stanford Research Systems, Sunnyvale, Calif.). The high electric field strength causes further expansion and charging of liquid droplets until very small (less than about 10 μm in diameter) sample droplets are formed. Desolvation of liquid droplets is aided by bathing the expansion jet with a 3 LPM heated Nitrogen gas counterflow. The analyte ions are extracted from the expansion jet by the HVA and pass into the glass capillary tube where they are infused into a 300 ml/min flow of Nitrogen carrier gas. The analyte and carrier gas then flows through to the DMS unit where it is analyzed.

Figure 2:
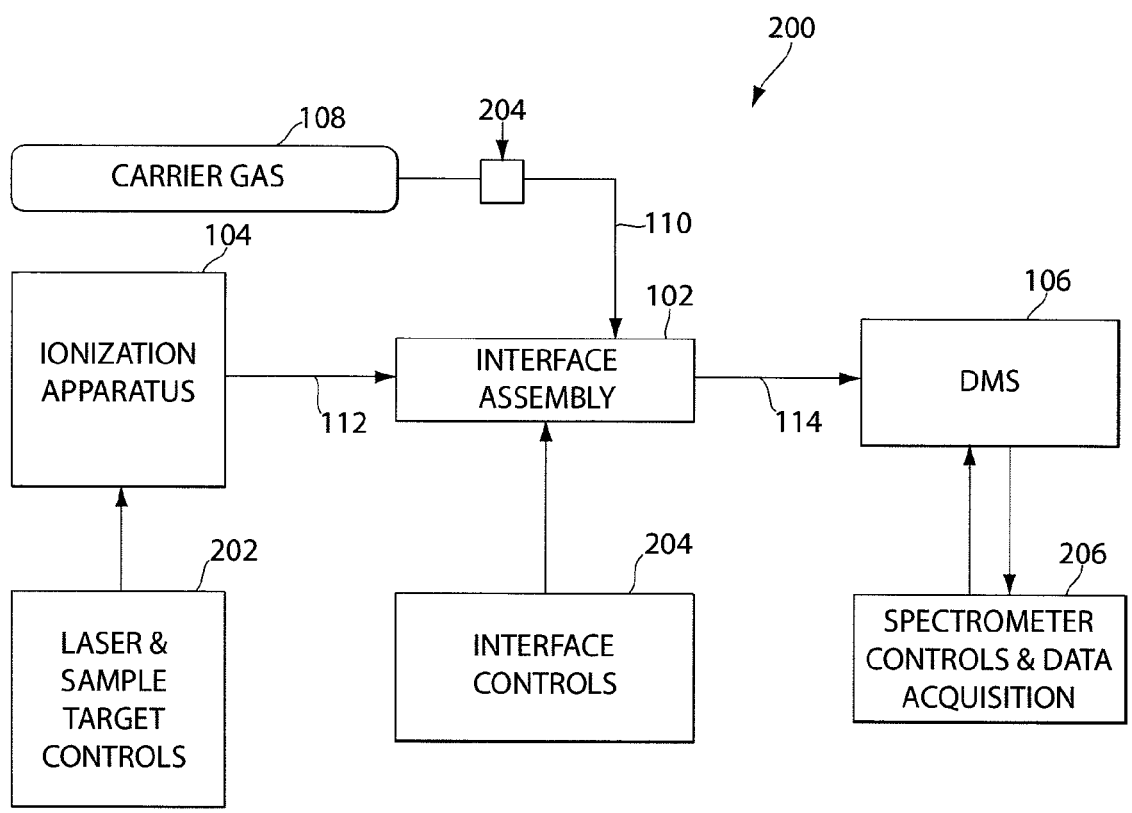
FIG. 2 is a block diagram of the system of FIG. 1, further representing a data flow path and control subsystem according to an illustrative embodiment of the invention.

FIG. 2 is a block diagram 200 of the system of FIG. 1, further representing a data flow path and control subsystem. The system may utilize one or more of the following control implements: where the ionization apparatus 104 is an AP-MALDI unit, positioning of the target plate and the activation of the UV laser in the AP-MALDI unit is controlled by computing means, such as, for example, a general-purpose computer (202); transport of the sample gas from the ionization apparatus 104 into the interface assembly 102 is controlled either electronically or mechanically, as described in more detail herein below (204); supply of a carrier gas 108 to the interface assembly 102 is implemented via a flow controller, such as, for example, a commercially-available digital mass flow controller (205); the DMS unit 106 is in communication with computing means, such as, for example, a general-purpose computer, for both instrument control and data acquisition (206).

Figure 3:
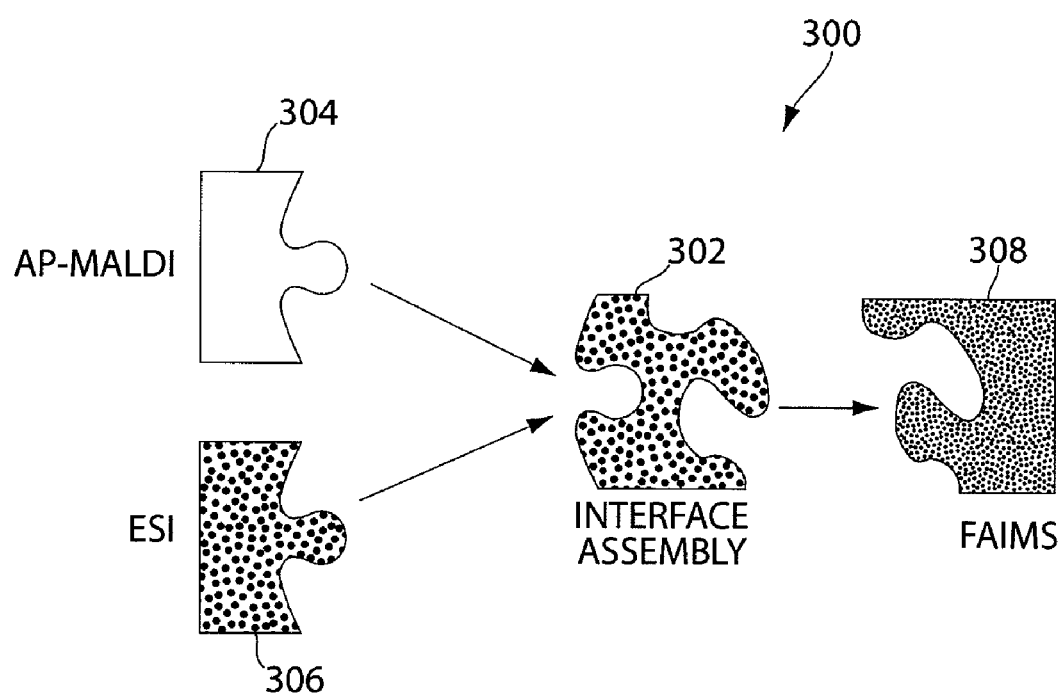
FIG. 3 is a schematic diagram that conceptually illustrates how the interface assembly provides for the interchangeability of two types of ionization apparatus—an ambient pressure matrix-assisted laser desorption ionization apparatus (AP-MALDI) and an electrospray ionization apparatus (ESI)—for operation with a field asymmetric ion mobility spectrometer (FAIMS), according to an illustrative embodiment of the invention.

FIG. 3 is a schematic diagram 300 that conceptually illustrates how the interface assembly 302 provides for the interchangeability of two types of ionization apparatus—for example, AP-MALDI 304 and ESI 306—for operation with the DMS (for example, a FAIMS 308). In one embodiment, the design of the interface takes into consideration the mechanical mating scheme used in Agilent Technologies Time-of-Flight Mass Spectrometer (TOF-MS, G1969A, Agilent Technologies, Palo Alto, Calif.) and uses a hinge-and-latch mechanism to easily interchange the two units. A customized ESI unit optimized for use with the DMS sensor is also contemplated herein.

Figure 4:
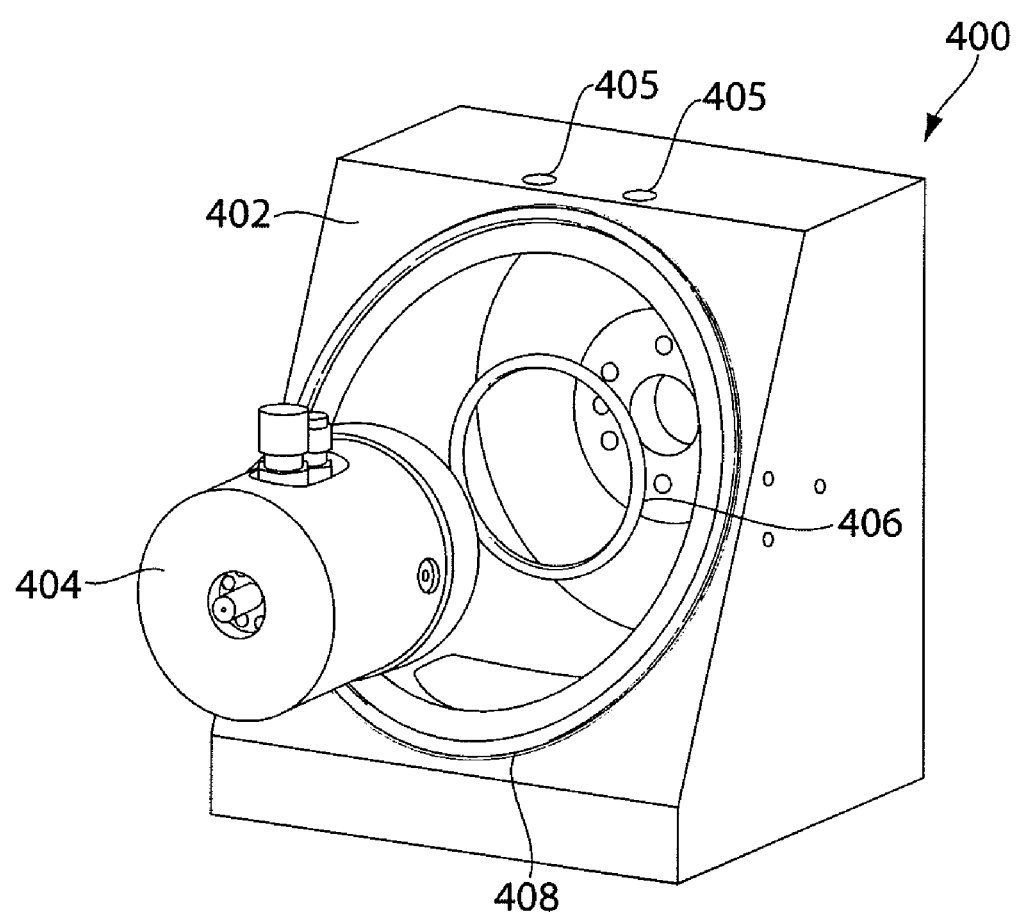
FIG. 4 is a diagram showing an exploded view of the interface assembly, according to an illustrative embodiment of the invention.

FIG. 4 is a diagram 400 showing an exploded view of the interface assembly in a preferred embodiment. The interface assembly has two major components—(1) the mount block 402, which provides mechanical support for the Sample-Detector Interface (SDI) 404, and is the mating platform between the ESI or AP-MALDI and the DMS, for example; and (2) the SDI 404, which draws and transports sample ions into the DMS sensor.

Figure 5A:
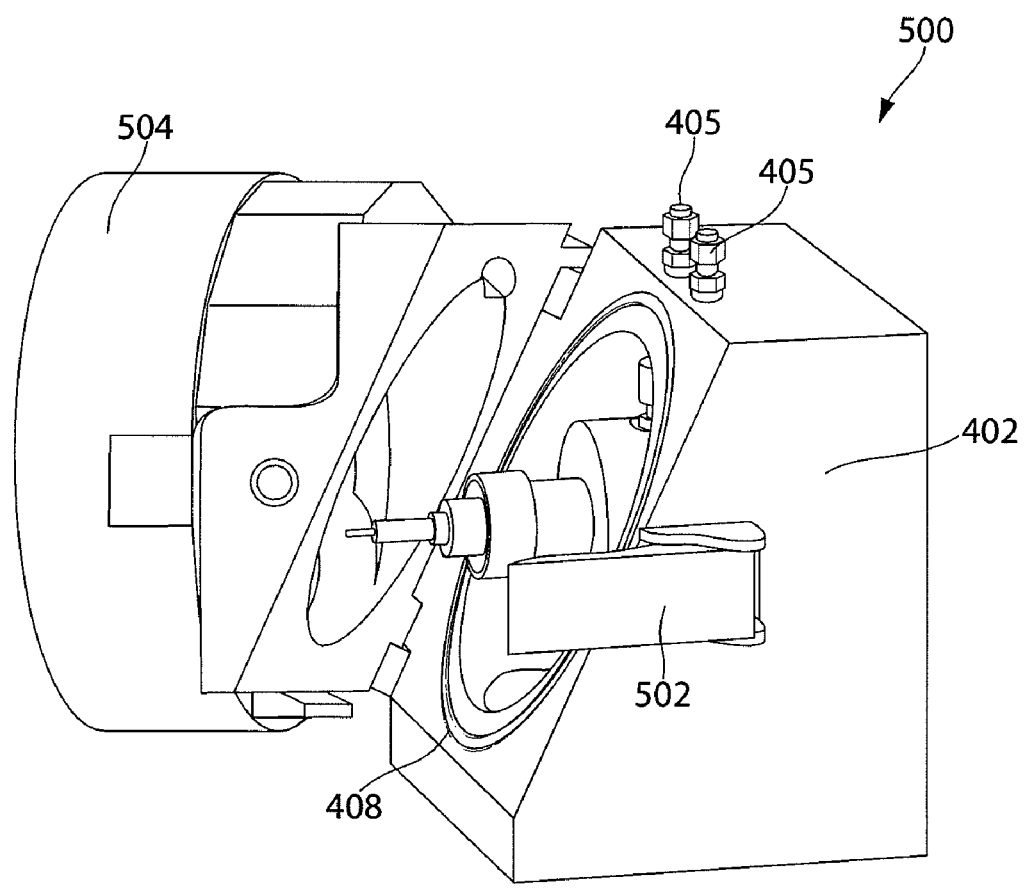
FIGS. 5A and 5B are diagrams showing how an AP-MALDI apparatus attaches to the interface assembly via a hinge-and-latch mechanism, according to an illustrative embodiment of the invention.
Figure 5B:
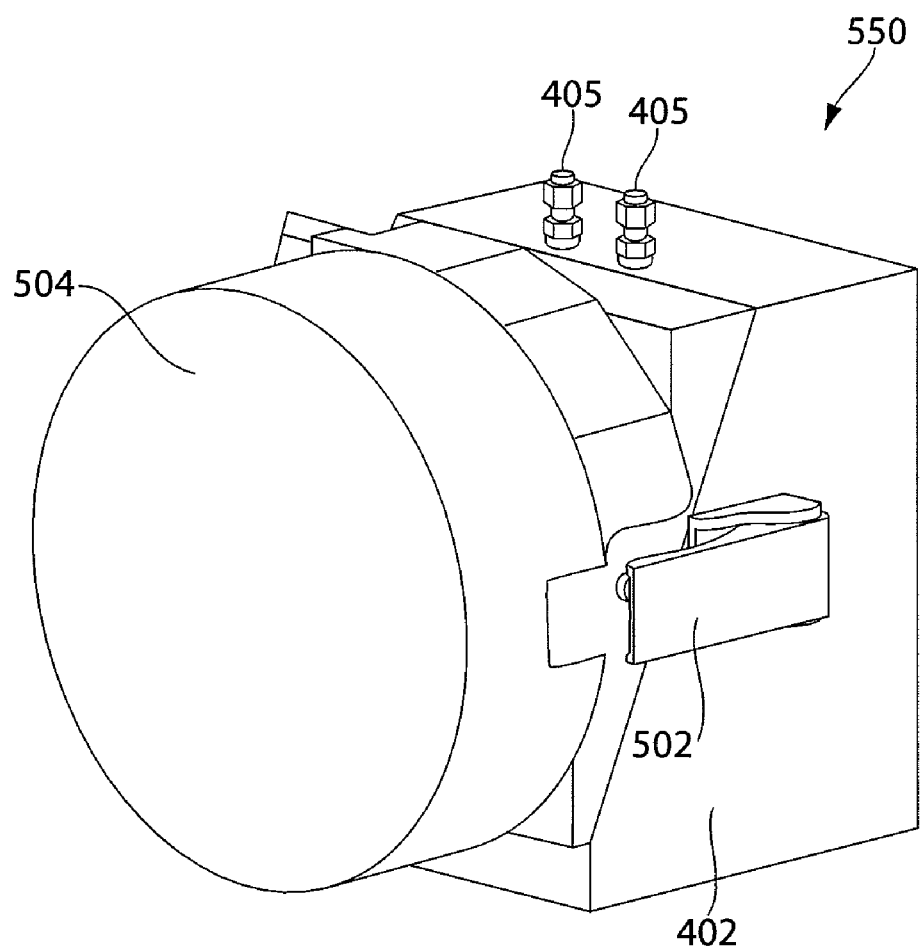

The mount block assembly 402 aligns the SDI to the ESI or AP-MALDI hardware, as shown in FIGS. 4, 5A, and 5B. Diagrams 500 and 550 of FIGS. 5A and 5B show how an AP-MALDI apparatus 504 attaches to the interface assembly via a hinge-and-latch mechanism on the mount block 402.

In one embodiment, the mount block 402 is constructed of grade 304 stainless steel, with rough dimensions of 5.4H× 4.75W×3.65D in. Two 1/16 in NPT threaded orifices 405 are machined into the top of the assembly to allow gas-tight plumbing for gases into the SDI. A third 1/8 in NPT threaded orifice was machined on one side of the assembly to include an electrical throughput for high voltage connection. The ESI or AP-MALDI units connect to the mount block 402 via a set of hinges located at the top and bottom of the mount block that allows the pins on the units to slide into the hinge orifices, as seen in FIG. 5. An o-ring 408 on the front face of the mount plate makes a gas-tight seal to the ESI or AP-MALDI unit, when compressed by a latch lever 502. For example, this hinge-and-latch mechanism allows easy attachment and interchange of the Agilent ESI or AP-MALDI units. Another o-ring 406 is used at the back end (the end that connects to the DMS) of the SDI to form a gas-tight seal between the SDI 404 and the mount block 402.

Figure 6:
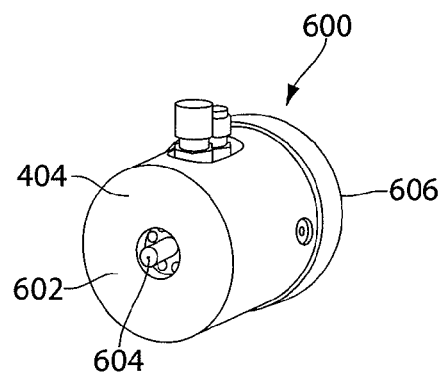
FIG. 6 is a diagram showing an assembled view of the sample-detector interface unit of the interface assembly, according to an illustrative embodiment of the invention.

FIG. 6 is a diagram 600 showing an assembled view of the sample-detector interface unit (SDI) of the interface assembly. The SDI 404, centrally aligned within the mount block 402, is an important component in ion transport into the DMS sensor from the ionization apparatus. This can be achieved in a three step process: 1) analyte ions are extracted from the ESI or AP-MALDI sample plume by an electrostatic field (602); 2) the sample-matrix mixture is dissolved by a heated gas to improve ion quality (604); and 3, ions are transported, with the aid of a carrier gas, to the DMS filter region (606). FIG. 6 shows the SDI unit 404 and indicates the locations of the above steps occurring during ion transport.

Figure 7:
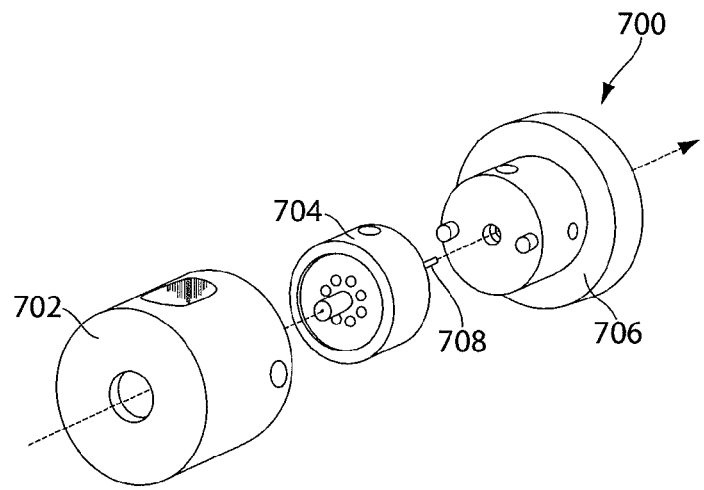
FIG. 7 is a diagram showing an exploded view of components of the sample-detector interface unit of the interface assembly, according to an illustrative embodiment of the invention.

Several components make up the SDI unit of the interface assembly as shown in the diagram 700 of FIG. 7. The SDI mount sleeve 702 holds the High Voltage Assembly 704 and Gas Manifold Assembly 706 together. Analyte ions pass through a glass capillary tube 708 in the middle of the SDI into the DMS sensor.

Figure 8:
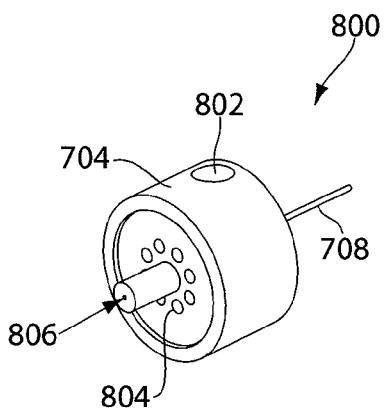
FIG. 8 is a diagram showing a high voltage assembly, one of the components of the sample-detector interface unit of the interface assembly, according to an illustrative embodiment of the invention.

The high voltage assembly (HVA) 704 is shown in the diagram 800 of FIG. 8. The HVA 704 consists of a 304ss drum concentrically housed by a Teflon insulation sleeve. Analyte ions enter the interface through a capillary inlet 806 with an orifice diameter, for example, of 800 µm. The area around the capillary inlet 806 is held at a high negative voltage in order to draw positively charged ions into the capillary. The Teflon sleeve and stainless steel drum are bored through to accept 1/16 in NPT plumbing for break-up gas flow 802. The break-up gas exits out the front end of the HVA 804 in a flow path opposite to that of the sample plume. High voltage connection to the stainless steel drum is achieved with a vacuum sealed, 1/8 in NPT electrical throughput rated at 5 kV, 1.8 A. Analyte ions pass from the capillary inlet 806 into a glass capillary (1 mm i.d.×10 cm) tube 708 into the Gas Manifold Assembly 706.

Figure 9A:
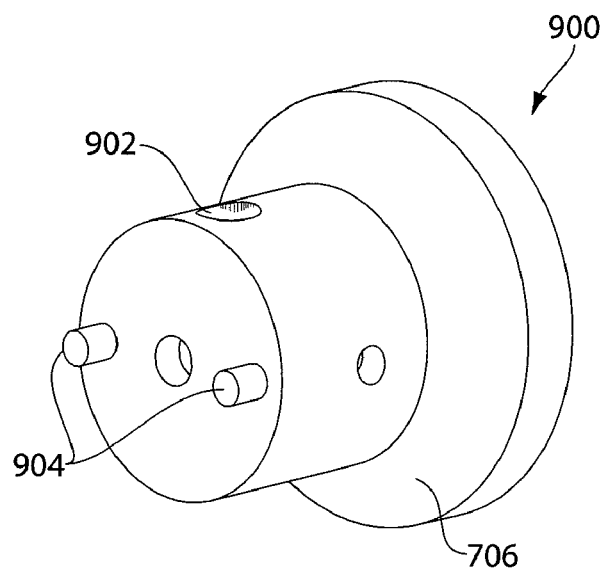
FIGS. 9A and 9B are diagrams showing front and rear views, respectively, of a gas manifold assembly, one of the components of the sample-detector interface unit of the interface assembly, according to an illustrative embodiment of the invention.
Figure 9B:
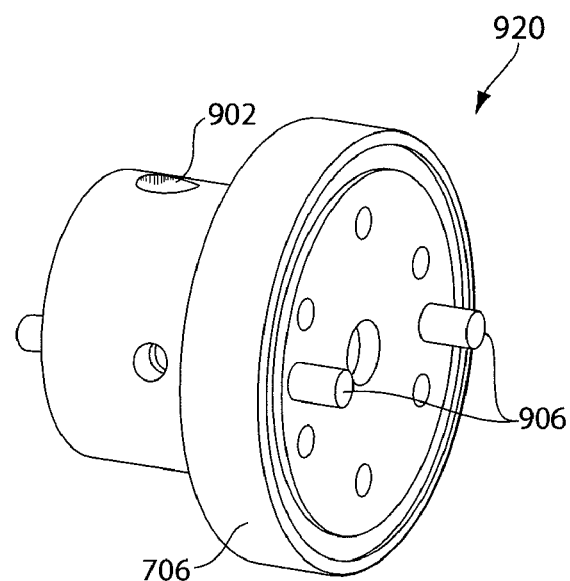

The Gas Manifold Assembly (GMA) 706 is shown in diagrams 900 and 920 of FIGS. 9A and 9B. The GMA 706 is designed so that a heated nitrogen gas envelops the analyte ion flow carrying it into the DMS sensor. The HVA 704 is aligned and mechanically attached to the GMA 706 employing Dowel pins 904. Three shoulder screws on the Mount Sleeve secure the HVA 704 and GMA 706 together. Another set of Dowel pins on the rear face of the GMA 706 locate this part to the Mount Block Assembly 402. A 1/16 in. NPT-threaded orifice 1102 machined into the top of the GMA 1102 (see FIG. 11) makes a gas-tight entrance for heated carrier gas flow into the SDI. Similarly, a 1/16 in. NPT-threaded orifice 802 is machined into the top of the HVA to make a gas-tight entrance for heated break-up gas flow into the SDI.

Figure 10:
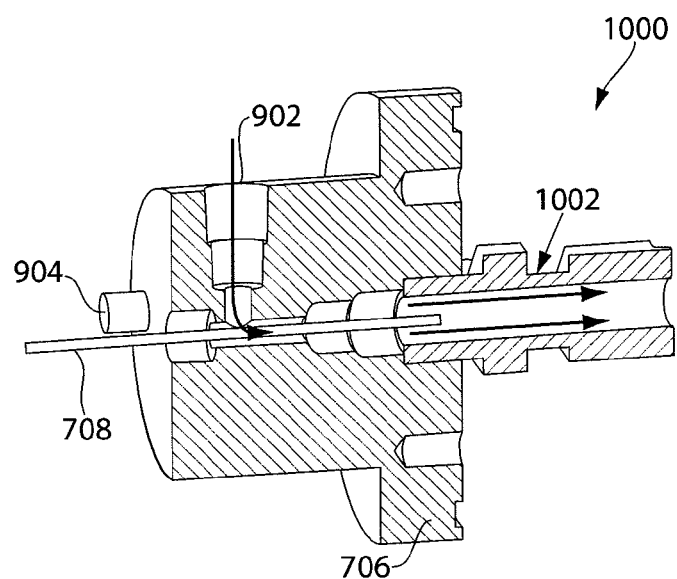
FIG. 10 is a diagram showing a cross-sectional view of the interface assembly, showing flow of carrier gas and ionized analyte into the ion mobility spectrometer, the ionized analyte coming from the ionization apparatus, according to an illustrative embodiment of the invention.

The diagram 1000 of FIG. 10 shows a cross-sectional view of the interface assembly and illustrates flow of a carrier gas through orifice 902 and flow of ionized analyte into the ion mobility spectrometer (DMS), the ionized analyte coming from the ionization apparatus. The glass capillary tube 708 extends past the nitrogen carrier gas flow entrance, allowing the gas to achieve laminar flow before being infused with the ion flow.

Figure 11:
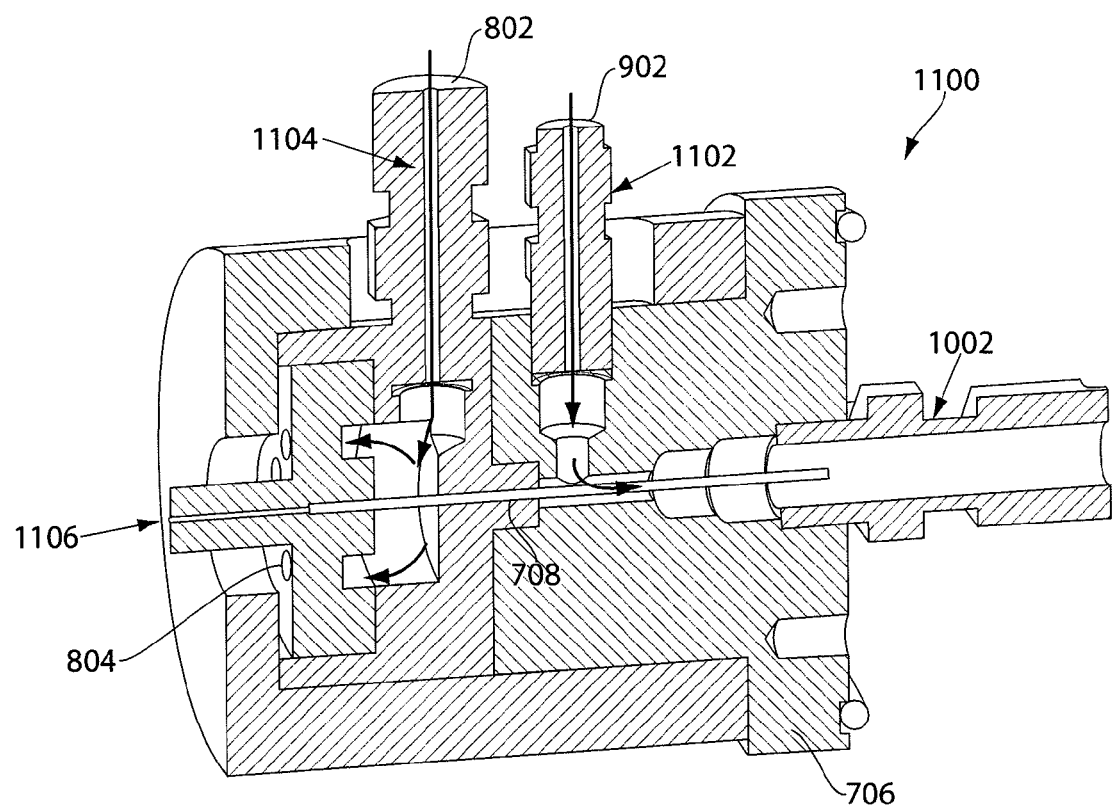
FIG. 11 is a diagram showing a cross-section view of the interface assembly adapted for the flow of a break-up gas located near the capillary inlet to break apart any sample clusters entering the interface assembly (i.e. matrix and analyte molecules), thereby providing a cleaner flow of analyte ions into the ion mobility spectrometer, according to an illustrative embodiment of the invention.

The diagram 1100 of FIG. 11 shows a cross-sectional view of the interface assembly adapted for the flow of a break-up gas located near the capillary inlet to break apart sample clusters entering the interface assembly at 1106 (i.e. matrix and analyte molecules), thereby providing a cleaner flow of analyte ions into the ion mobility spectrometer. Overall ion and gas flow through the entire SDI unit is depicted in FIG. 11. The entire length of the SDI is approximately 6 cm. The rear of the SDI unit accepts a 1/8 in NPT straight union 1002 for direct connection to the DMS sensor.

Figure 12A:
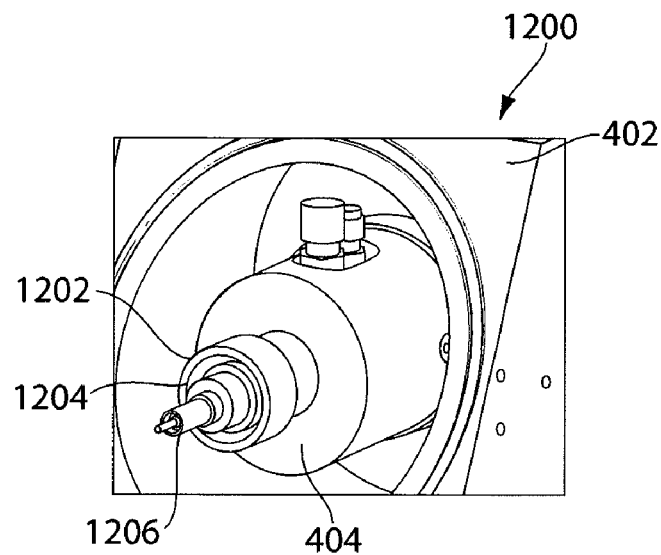
FIG. 12A is a diagram showing how capillary inlet components of the interface assembly may be adapted for use of AP-MALDI as the ionization apparatus, according to an illustrative embodiment of the invention.
Figure 12B:
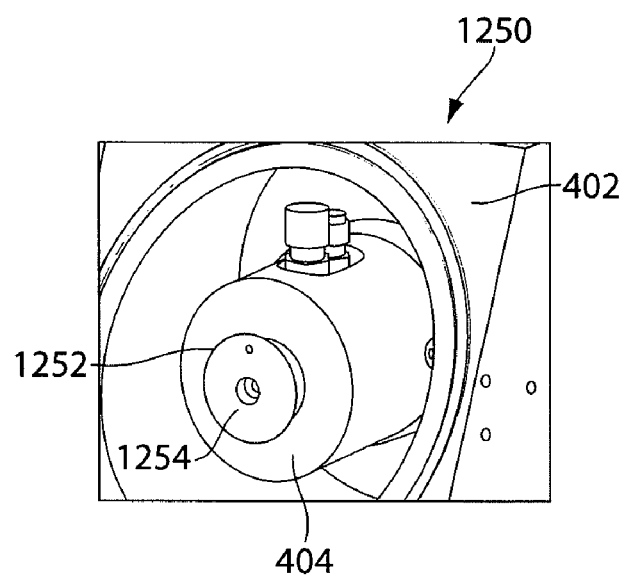
FIG. 12B is a diagram showing how capillary inlet components of the interface assembly may be adapted for use of ESI as the ionization apparatus, according to an illustrative embodiment of the invention.

The Agilent AP-MALDI and ESI units utilize a slightly different sample introduction-to-capillary inlet components. The SDI is designed so that these commercially available components can be used with our interface and are easily interchanged, as shown in the diagrams 1200 and 1250 of FIGS. 12A and 12B. FIG. 12A shows the SDI with AP-MALDI capillary interface components: Teflon high voltage insulator 1202; break-up gas cylinder 1204; and capillary extension 1206. FIG. 12B shows the SDI with ESI capillary interface components: break-up gas outlet 1252; and glass capillary inlet 1254.

Figure 13:
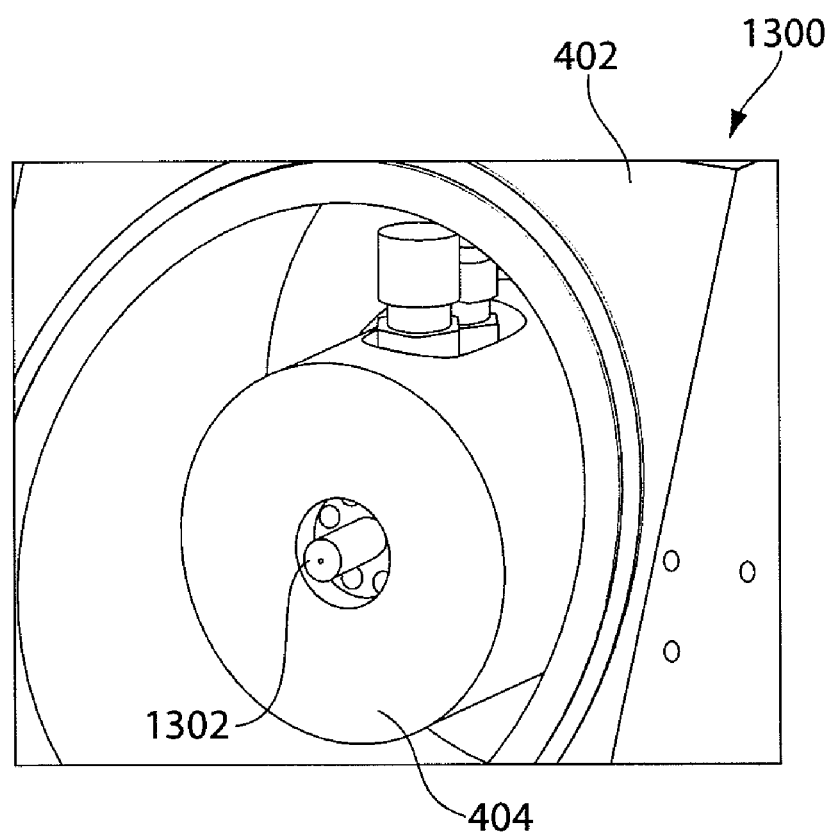
FIG. 13 is a diagram showing a high voltage capillary interface mount for attachment of either of the capillary inlet components shown in FIGS. 12A and 12B, according to an illustrative embodiment of the invention.

Both sets of components can be screwed into the high voltage capillary interface mount 1302 on the front of the SDI (diagram 1300 of FIG. 13), and are secured by a gold spring. This is an electrically conductive contact, and is held at a high bias to attract ions.

In one embodiment, the ESI-DMS (or AP-MALDI-DMS) interface is modified to allow a higher voltage to be applied to the outer capillary tube shield. In a preferred embodiment, the metal surrounding the entrance to the high voltage capillary shield also is connected to a relatively high potential (although in alternative embodiments, it is connected to ground). The modified application of high voltages creates a stronger, more directed electric field that extracts more ions from the ESI (or AP-MALDI) plume, and accelerates them into the inlet of the DMS (i.e. FAIMS) sensor.

Figure 14:
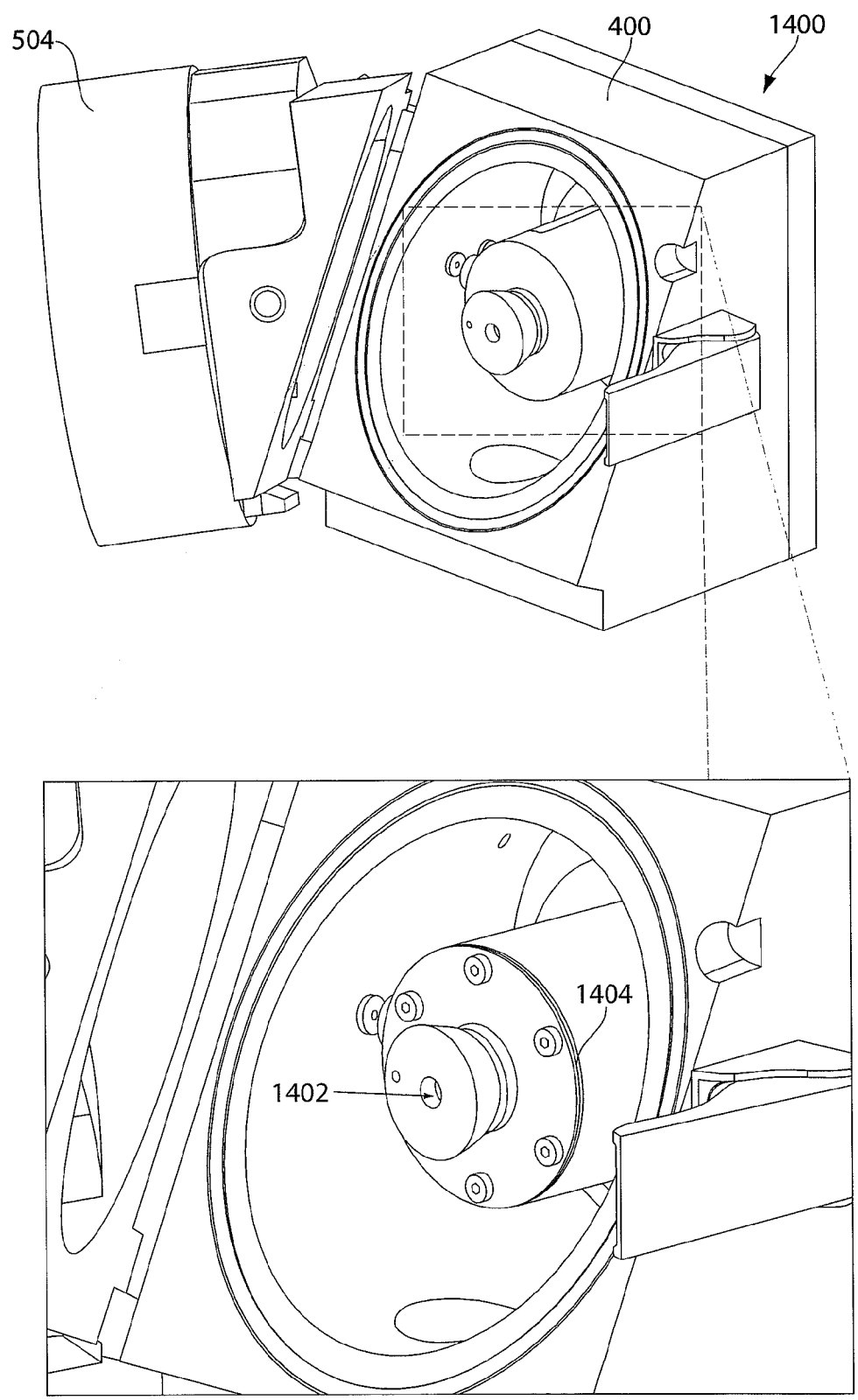
FIG. 14 is a schematic diagram showing a voltage divider that allows application of different voltages to the capillary shield and the inner capillary tube of the interface assembly, according to an illustrative embodiment of the invention.

A layer of Teflon insulation 1404 may be added in between the capillary shield and the rest of the interface to electrically isolate the capillary shield 1402, as shown in the diagram 1400 of FIG. 14. Because the Teflon insulation is positioned between two elements of different electric potentials, the thickness of the insulation should be sufficient to prevent breakdown of the material from occurring. The dielectric strength of Teflon is 1500 kV/inch. Based on restrictions of part sizes in the interface, a Teflon insulating shield 43 mm in thickness can isolate the external capillary shield 1402 from the rest of the interface.

A voltage divider may apply different voltages to the capillary shield 1402 and the inner capillary tube using a single power supply. For example, when the inner capillary is connected to a voltage of −3.2 kV, the voltage on the outer capillary shield can be adjusted between −1.5 and −3.1 V. The voltage divider offers flexibility in generating a wide range of voltages, thus enabling optimization.

FIGS. 15A to 15D are schematic diagrams 1500, 1520; 1550, 1570 illustrating steps in a method of analyzing a sample, the method utilizing the interface assembly for delivering ionized sample from an AP-MALDI unit into an ion mobility spectrometer.

Figure 15A:
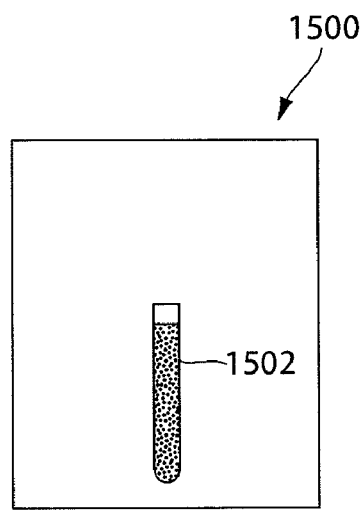
FIGS. 15A-15D are schematic diagrams illustrating steps in a method of analyzing a sample, the method utilizing an interface assembly for delivering ionized sample from an AP-MALDI unit into an ion mobility spectrometer, according to an illustrative embodiment of the invention.

Diagram 1500 of FIG. 15A shows the solid or liquid sample is dissolved in MALDI matrix solution. The matrix solution contains a solvent, such as, for example, water or methanol, and a UV-absorbing compound. In commercially-available MALDI matrix solutions, the UV-absorbing compound is often an organic acid, such as, for example, 2,5-dihydroxybenzoic acid, sinapinic acid, or α-cyano-4-hydroxycinnamic acid.

Figure 15B:
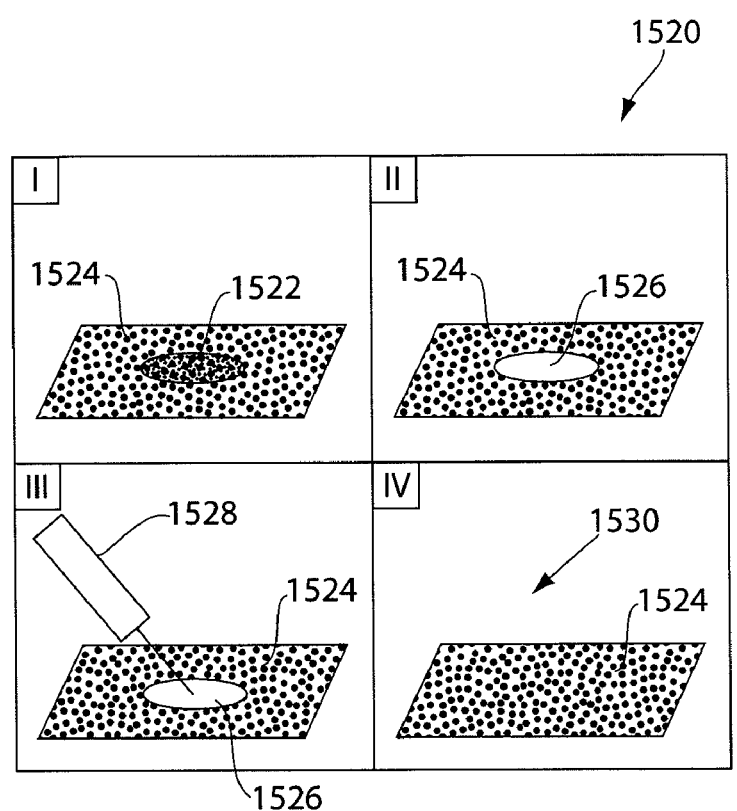

Box (i) of FIG. 15B shows the resulting solution 1522 is deposited onto the target plate 1524 in the AP-MALDI unit. In many embodiments, the sample concentration is usually at or below 1 pmol/µl. In some embodiments, the solution is deposited on the target plate manually by a pipette. Some commercially-available AP-MALDI units, such as G1972A unit (Agilent Technologies, Palo Alto, Calif.) are equipped with target plates allowing up to 96 different samples to be loaded and desorbed in sequence. In other embodiments, sample loading is implemented using an automated robotic pipetting system. In yet other embodiments, microfluidic sample loading systems are employed. Then, in box (ii) of FIG. 15B, the solvent is allowed to evaporate from the sample-matrix solution, leaving a sample matrix solid 1526. In some embodiments, the evaporation is accelerated by a heated nitrogen gas stream. Next, in box (iii), the sample-matrix solid 1526 is exposed to the UV laser 1528. One commercially available system (available from Agilent of Palo Alto, Calif.) uses a nitrogen laser with a wavelength of 337 nm. As a result of such exposure, the matrix absorbs energy from the laser. Some energy is transferred to sample molecules. The energy causes the matrix and sample molecules to desorb from the plate and become ionized 1530, as shown in box (iv) of FIG. 15B.

Figure 15C:
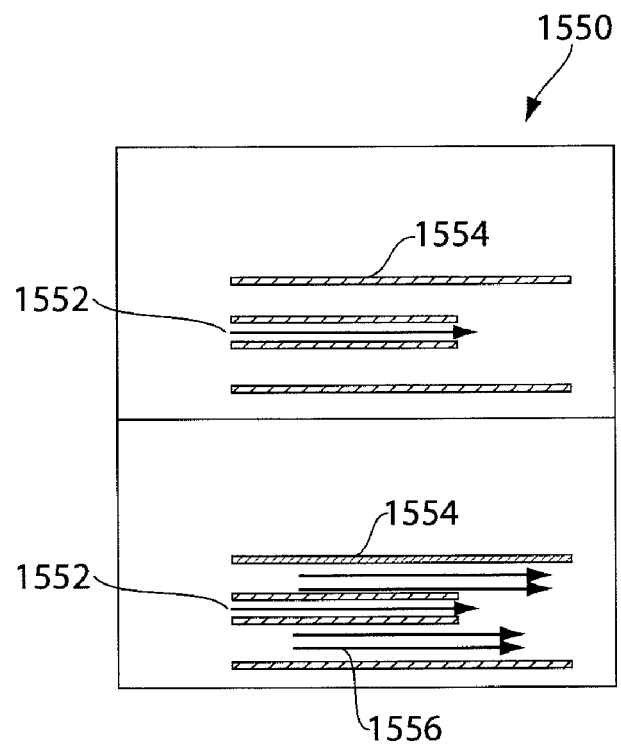

Transport of the sample gas from the AP-MALDI unit into the AP-MALDI-DMS interface assembly is controlled either electronically, mechanically, or using both electrical and mechanical methods. In an electrical method, the ionized sample is drawn into the AP-MALDI-DMS interface module using a high voltage opposite to ion polarity. In some commercially available devices, a potential of typically 1-5 kV is used to accelerate the sample gas from the AP-MALDI into the detector. In a mechanical method, the ionized sample is pushed/drawn into the next stage using a pressure differential. A carrier gas (such as nitrogen) is introduced into the chamber near the target plate. The carrier and sample gases are then drawn out of the AP-MALDI unit and into the AP-MALDI-DMS interface module using a pressure drop. FIG. 15C shows a channel 1554 of the interface assembly. The bottom box of FIG. 15C shows how sample-matrix gas 1552 is infused into a carrier gas flow 1556.

Figure 15D:
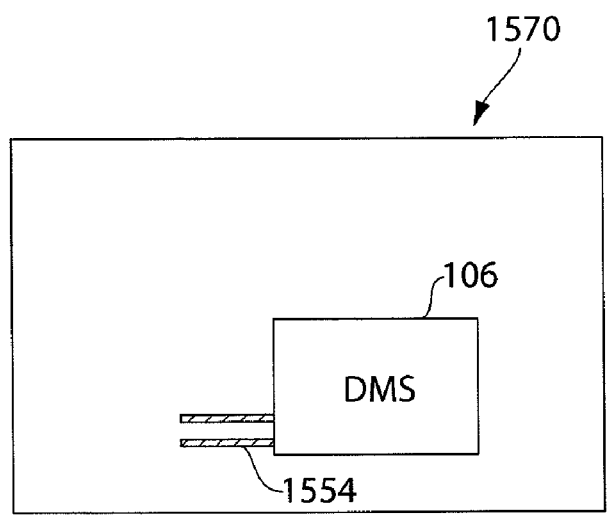

Once received in the interface module, the sample-matrix gas is infused into a carrier gas flow and directed to flow through the DMS unit 106, where detection takes place, as shown in the diagram 1570 of FIG. 15D.

Additional applications of differential mobility spectroscopy that may be used with the apparatus, systems, and methods described herein are disclosed in the following co-owned U.S. patent applications: U.S. patent application Ser. No. 10/817,455 filed Apr. 1, 2004; U.S. Patent Application No. 60/678,080 filed May 5, 2005; U.S. Patent Application No. 60/692,103 filed Jun. 20, 2005; U.S. Patent Application No. 60/692,836 filed Jun. 22, 2005; U.S. Patent Application No. 60/695,291 filed Jun. 30, 2005; and U.S. Patent Application No. 60/697,132 filed Jul. 7, 2005, all of which are hereby incorporated by reference, in their entirety.

EXPERIMENTAL EXAMPLES

Experiments were conducted to demonstrate the workability of various embodiments of the invention. In the experiments, ESI and AP-MALDI systems, manufactured by Agilent Technologies of Palo Alto, Calif., were used. These units are described in more detail hereinabove, and operational details are described hereinbelow with respect to each experiment. The experiments use the AP-MALDI matrix, α-cyano-2-hydroxycinnamic acid, manufactured by Agilent Technologies. The experiments also use methyl tert-butyl ether, product number 306975, manufactured by Sigma Aldrich; the protein, bovine serum albumin (BSA), product number A7638, manufactured by Sigma Aldrich; and the protein, ubiquitin, product number U-6253, manufactured by Sigma Aldrich.

Figure 16:
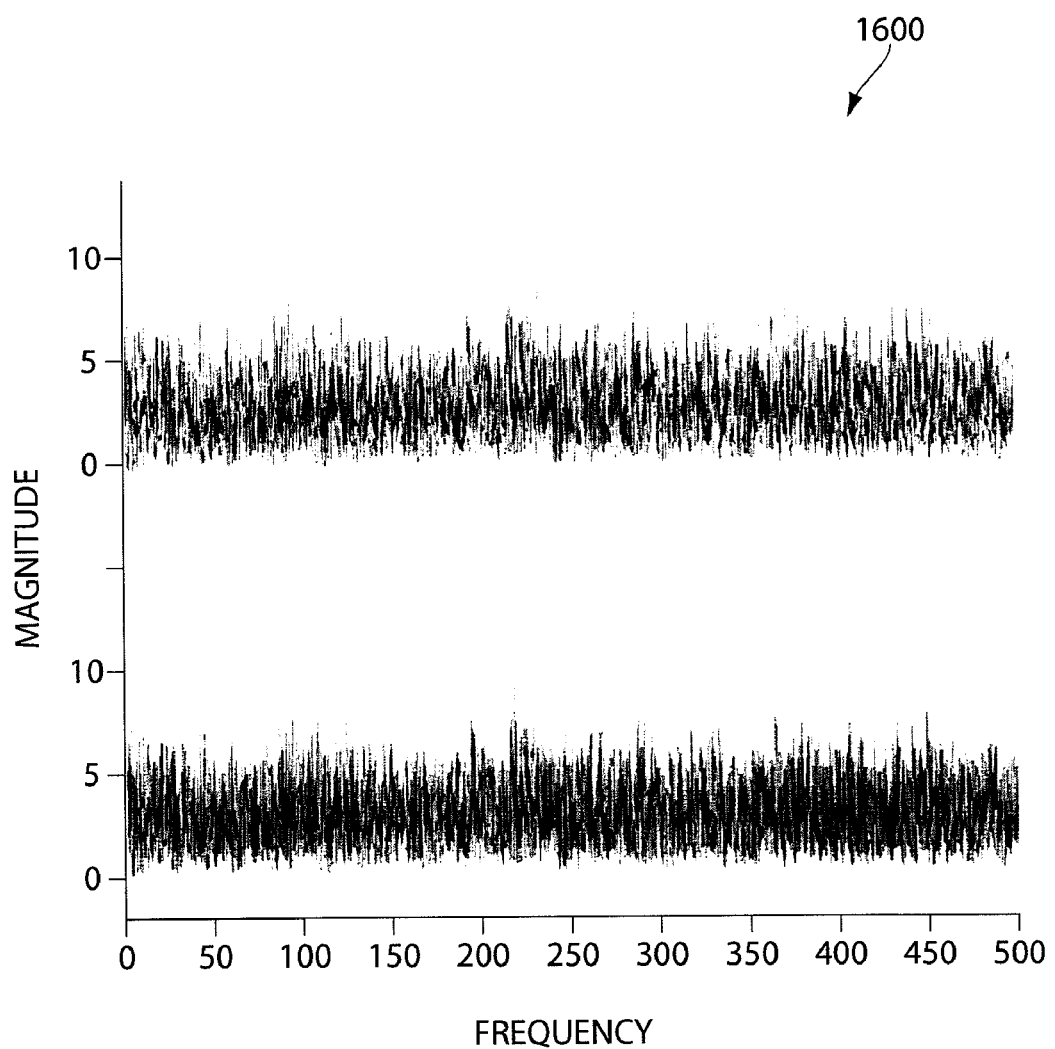
FIG. 16 is a graph showing Fourier transform plots of concatenated AP-MALDI/FAIMS spectra of α-cyano-2-hydroxycinnamic acid and a blank, using the interface assembly according to an illustrative embodiment of the invention.

Experiment 1: AP-MALDI-FAIMS (DMS) Experiment with α-Cyano-2-Hydroxycinnamic Acid An example of AP-MALDI-DMS operation was conducted with α-cyano-2-hydroxycinnamic acid, a matrix substance used in AP-MALDI. A small area of 2 μg crystallized α-cyano-2-hydroxycinnamic acid was ablated and introduced into the DMS sensor. FIG. 16 is a graph 1600 showing Fourier transform plots of concatenated spectra of α-cyano-2-hydroxycinnamic acid and a blank, using the above-described interface assembly (without the voltage divider setup shown in FIG. 14). The red and green traces in FIG. 16 were produced by applying the Fast Fourier Transform algorithm to calculate the Discrete Fourier Transform of a chronologically concatenated vector of DMS scans. The graph 1600 shows the magnitude of the first 500 hundred calculated frequency values produced by the transform operation. The green trace represents the magnitude of the transform of data taken when α-cyano-2-hydroxycinnamic acid was ablated, while the red line represents the magnitude of the transform of data taken when a blank area was ablated (background). Two overlays of these transforms are shown on the same plot for comparison purposes. The upper overlay shows the sample transform on top of the background transform, and the lower overlay shows the same background transform on top of the sample transform.

In addition to an upward shift observed in the sample transform, the overlays show that the amplitude of the sample transform is slightly higher than the amplitude of the blank/background transform, indicating that there is more power/information in the data collected when matrix is ablated. The magnitude and phase plots of the Fourier transform are unique to the original signal, and can be used to faithfully reconstruct the original data—this transformation preserves all information present in the original data, but provides a different perspective on the data.

Experiment 2: ESI-FAIMS (DMS) Experiment with Methyl Tert-Butyl Ether

Figure 17:
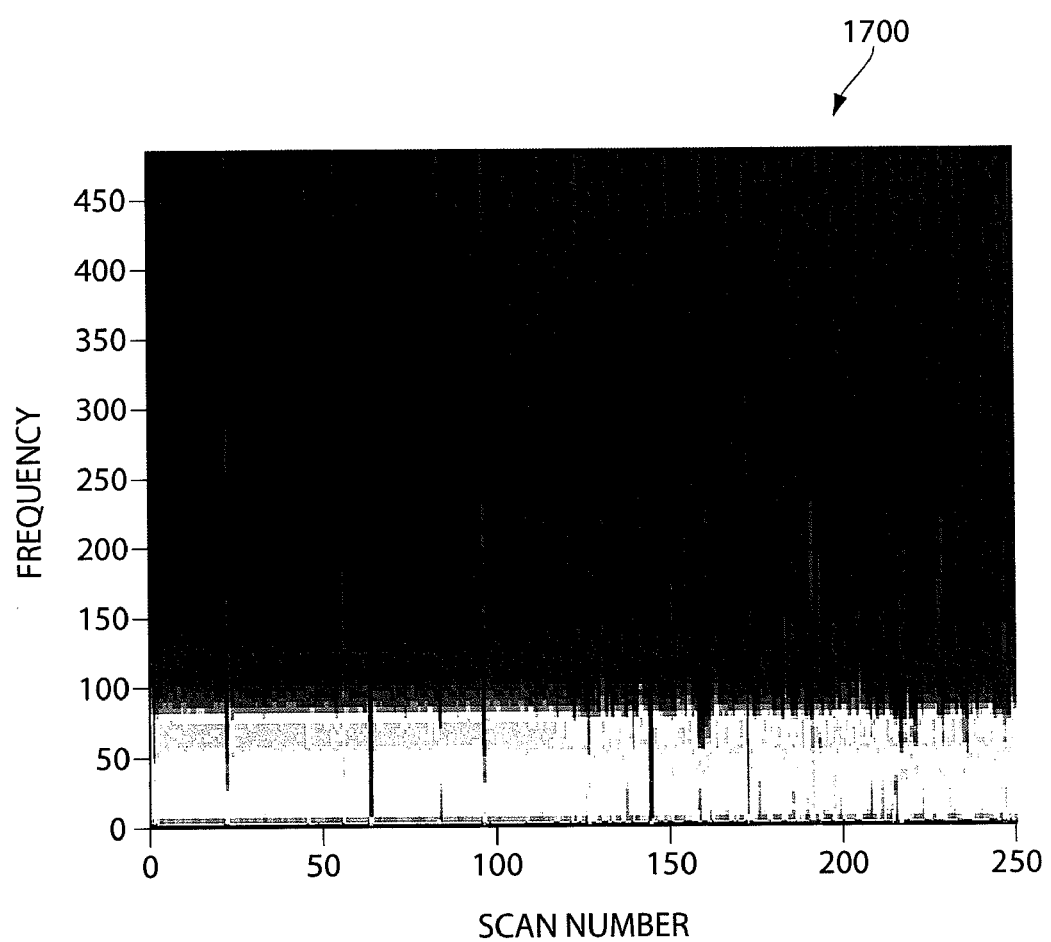
FIG. 17 is a graph showing a Fourier transform plot of ESI/FAIMS spectra of 10 μM methyl tert-butyl ether in water, using the interface assembly according to an illustrative embodiment of the invention.
Figure 18:
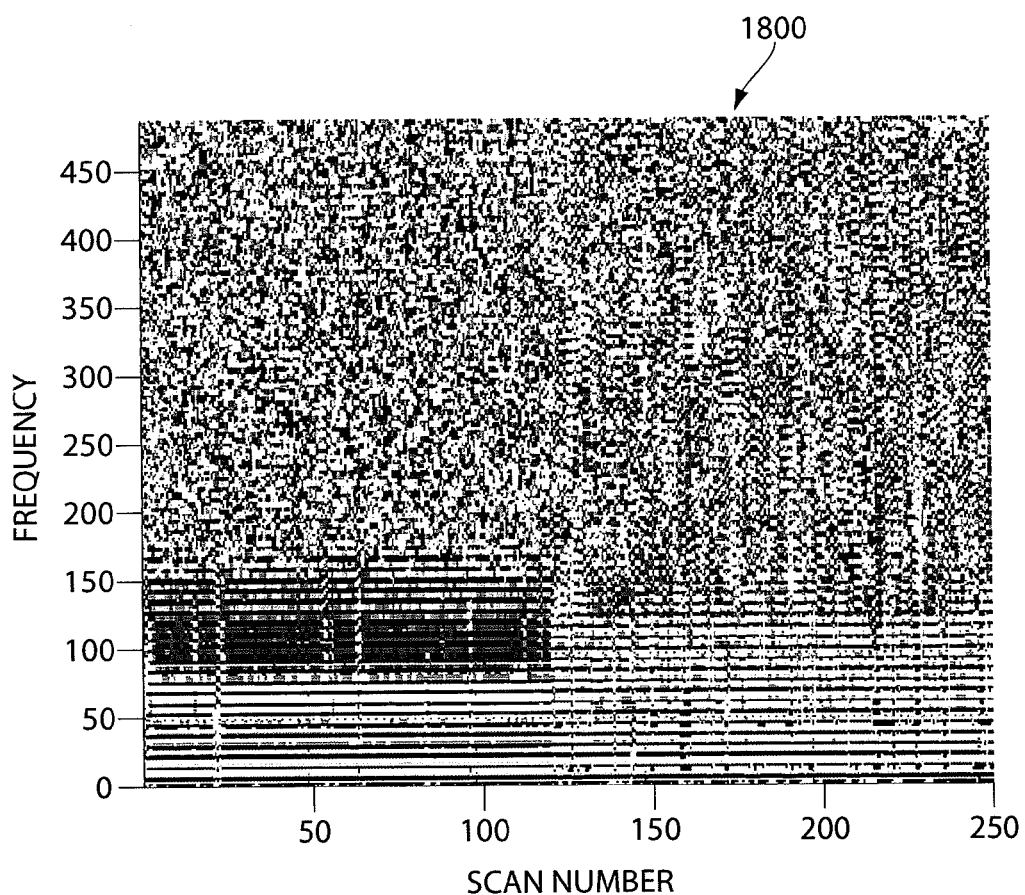
FIG. 18 is a graph showing the phase of the ESI/FAIMS Fourier transform plot of FIG. 17, according to an illustrative embodiment of the invention.

ESI-DMS spectra of various organic and biological molecules including methyl t-butyl ether, desmosine, urea, bovine serum albumin (BSA), and leucine-enkephalin have been obtained (only results with methyl tert-butyl ether in water are shown in FIGS. 17 and 18). FIG. 17 is a graph showing a Fourier transform plot 1700 of ESI/FAIMS spectral of 10 μM solution of methyl tert-butyl ether in water, using the interface assembly described hereinabove.

The x-axis corresponds to the scans taken during the entire DMS analysis. Scans 0-60 are DMS background with all other components off. During scans 60-120, the high voltage on the HVA was turned on; the sample began infusion into the ESI needle, and subsequently the DMS, during scans 120-190. From 190-250, the high voltage of the orifice was turned off. As can be seen, a change in the plot around scan 120 is observed. This response corresponds to the time when sample was being introduced into the ESI-DMS system. The ESI-DMS response to methyl tert-butyl ether is further elucidated by plotting the phase of the Fourier transform of the methyl tert-butyl ether DMS spectra, as shown in the graph 1800 of FIG. 18. Again, a clear change in response is observed at scan 120, when sample was being introduced into the DMS unit.

Experiment 3: AP-MALDI—FAIMS (DMS) Experiment with α-Cyano-2-Hydroxycinnamic Acid, Using Voltage Divider Setup Shown in FIG. 14

Experiments demonstrating AP-MALDI-DMS operation with the voltage divider setup shown in FIG. 14 were performed. Experimental conditions are summarized in Table 1. The RF voltage of the FAIMS sensor was set to +1400 V to allow for maximum ion separation and filtration, and compensation voltage was set to scan across a voltage range of −40 V to +10 V DC in 250 steps of 0.2 V.

TABLE 1

Experimental conditions for AP-MALDI - FAIMS(DMS) experiment with α-cyano-2-hydroxycinnamic acid, using voltage divider setup shown in FIG. 14.

| System Parameters | Experiment condition |
| --- | --- |
| Carrier Gas Flow Rate | 350 ml/min |
| Carrier Gas Heater | On |
| Break Up gas Flow Rate | 1.5 L/min |
| Break Up Gas Heater | Off |
| Pump Flow Rate | 500 ml/min |
| Extraction Voltage | −3000 V |
| RF Voltage | 1400 V |

Figure 19:
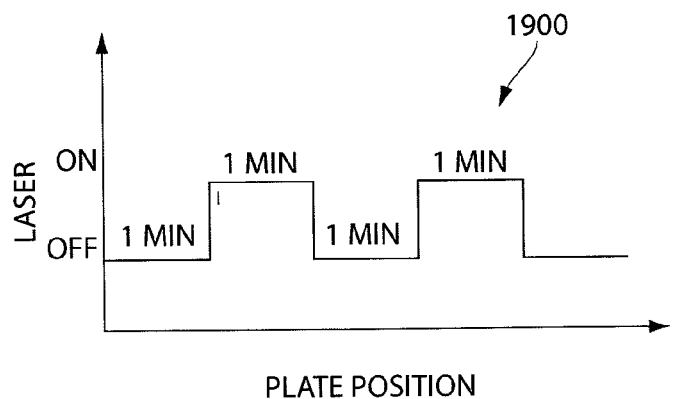
FIG. 19 is a graph illustrating laser operation in a data collection procedure for AP-MALDI/FAIMS analysis of a sample, using the interface assembly equipped with the voltage divider of FIG. 14, according to an illustrative embodiment of the invention.

Data was collected in the following sequence: collection of background FAIMS signal for 1 minute, laser ablation on clean plate surface for 1 minute, background collection for 1 minute, and then laser ablation on plate with sample for 1 minute, as shown in the graph 1900 of FIG. 19. Each sequence was replicated 5 times per sample type. Data was collected when the laser was off and when firing on a clean surface of the target plate so that the effects of laser fire could be isolated from the data obtained when a sample was ablated. By collecting data for different conditions of the laser and the plate, the ion signal could be discerned from possible background noise rising from the laser or target plate surface contaminants.

Figures 20A, 20B, 20C:
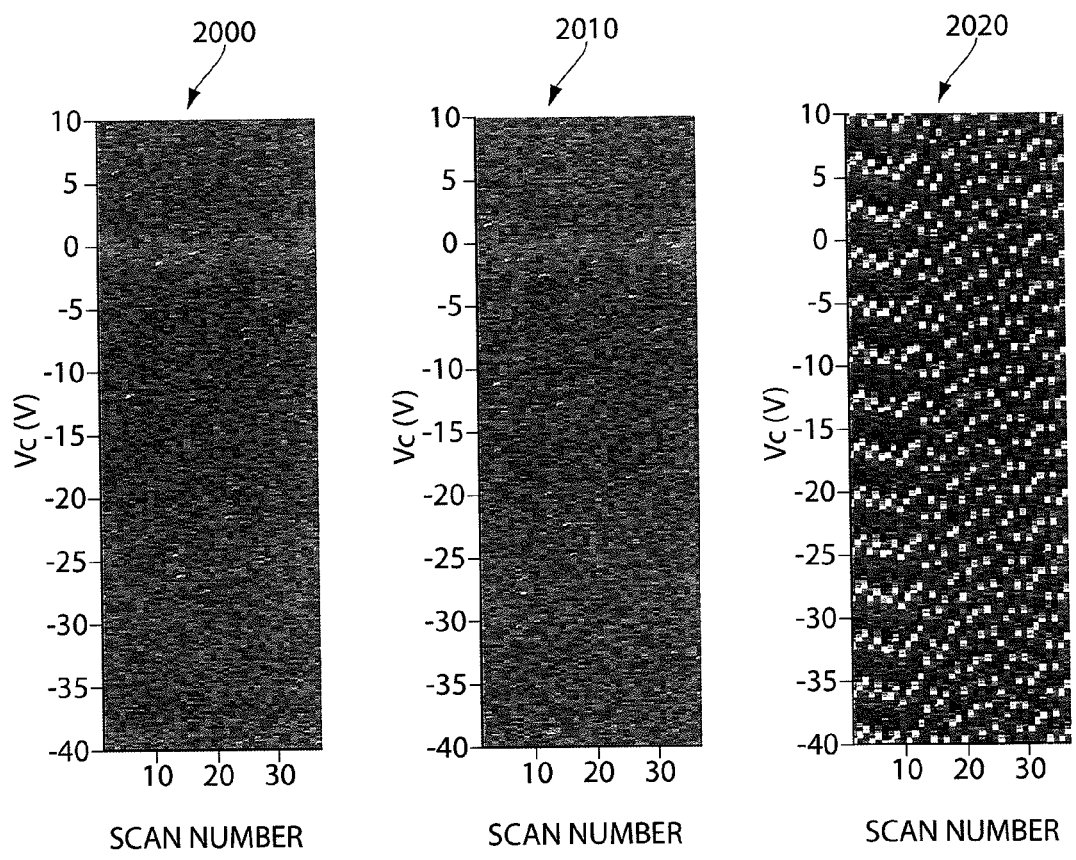
FIGS. 20A-20C are graphs showing ion spectra obtained using the AP-MALDI/FAIMS system with the interface assembly, where

Results from this testing indicated there was a clear change in the FAIMS spectra from the background signal during the time when the laser ablated plate areas that contained sample-matrix mixtures. AP-MALDI-FAIMS data can be visualized as a three dimensional plot where the horizontal axis is time, measured in scan numbers (1.5 sec/scan), and the vertical axis is the compensation voltage axis. The intensity of the pixel color for any given time and compensation voltage pair refers to the ion abundance detected. 3-dimensional plots of data 2000, 2010, and 2020 are shown in FIGS. 20A-20C. FIG. 20A shows a plot of data 2000 corresponding to FAIMS signal recorded when the laser is turned off. FIG. 20B shows a plot of data 2010 corresponding to a signal recorded when a blank or unspotted area of the target plate was ablated. As can be seen, there is no noticeable change from the background data in FIG. 20A. FIG. 20C shows a plot of data 2020 corresponding to a signal recorded during laser ablation of a sample spot on the target plate. There is a clear difference in the data—roughly 12-14 peaks per scan—from data taken when sample was not ablated. The presence of clear changes in signal when sample was ablated is evidence that AP-MALDI ionized substances are successfully being introduced into the FAIMS via the custom interface.

Experiment 4: ESI-FAIMS (DMS) Experiment with the Protein, Ubiquitin, Using Voltage Divider Setup Shown in FIG. 14

Operation of the ESI-FAIMS interface has enabled collection of experimental data to develop sophisticated bioinformatics approaches for data analysis. The surrogate proteins, bovine serum albumin (BSA) and ubiquitin were employed to collect replicate injections (results are shown for ubiquitin only). The ESI-FAIMS operational parameters used for these experiments are summarized in Table 2.

TABLE 2

Experimental conditions for ESI - FAIMS(DMS) experiments with bovine serum albumin (BSA) and ubiquitin, using voltage divider setup shown in FIG. 14.

| Parameter | Tested Settings |
| --- | --- |
| Carrier gas rate | 50 ml/min |
| Carrier gas temperature | On |
| Breakup gas rate | 3 LPM |
| Breakup gas temperature | On |
| Nebulization gas rate | 1 LPM |
| Vacuum pressure | Measured daily at approximately 753 Torr |
| Vacuum flow rate | 500 ml/min |
| Extraction voltage | −3.52 kV |
| RF voltage | 1400 V |
| Ni-63 source | Shielded or unshielded |
| Sample infusion rate | 20 μl/min |
| Protein concentration | 50 μg/ml |

Figure 21A:
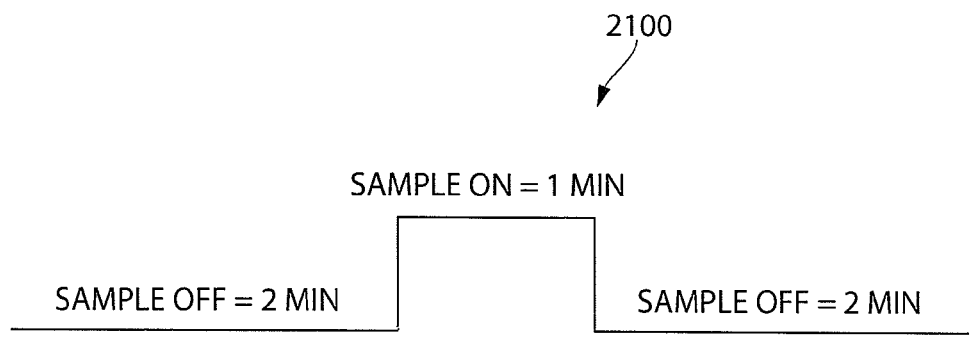
FIGS. 21A and 21B are a graph illustrating ESI operation in a data collection procedure for ESI/FAIMS analysis of a sample, using the interface assembly equipped with the voltage divider of FIG. 14, according to an illustrative embodiment of the invention.

ESI sampling was conducted in on/off cycles which consisted of the time during which the proteins were nebulized/ionized (sample on) and a $N_2$ only purging cycle (sample off), as shown in the schematic 2100 of FIG. 21A. A complete cycle corresponded to one replicate (see inset 2120 of FIG. 21B—demonstrates one complete cycle).

Figure 21B:
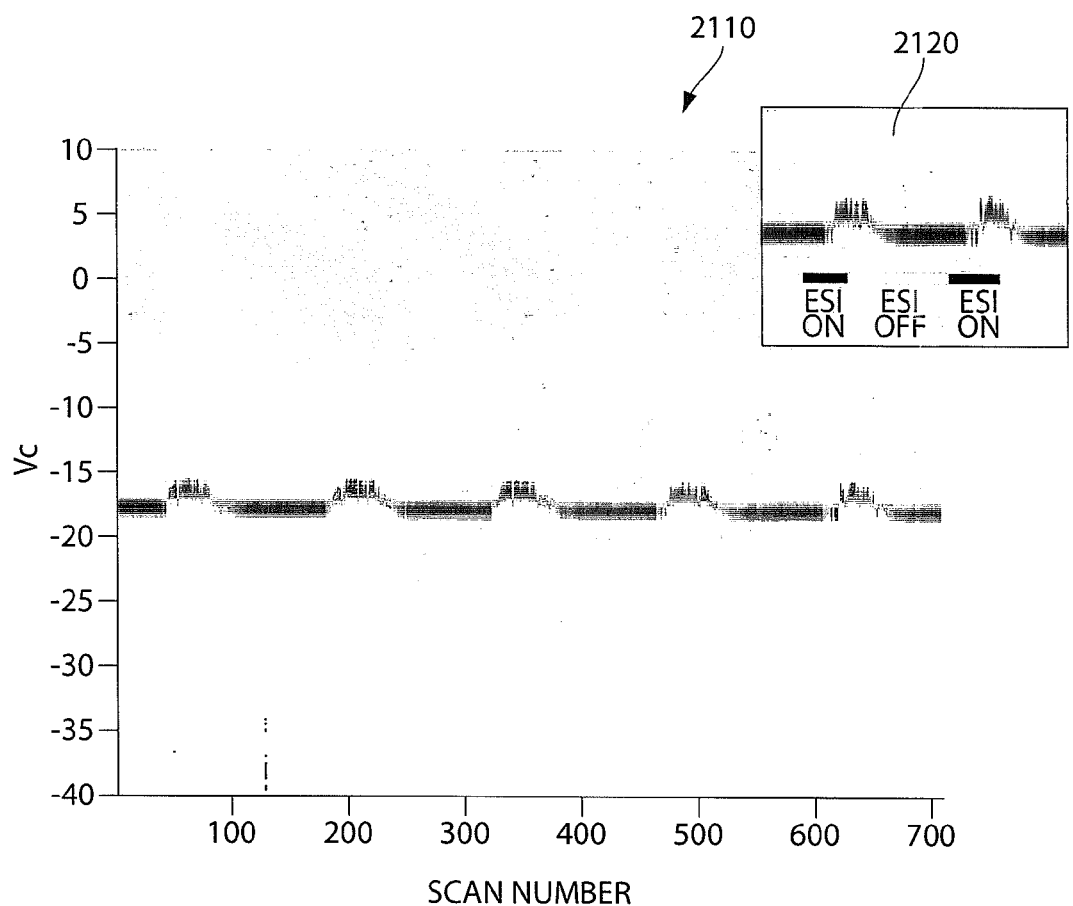

The purging cycle enables the system to clean and recover to a typical baseline level. As can be seen from the graph 2110 of FIG. 21B, a shift in the Reactant Ion Peak is observed only when the sample is being introduced through the ESI interface to the FAIMS; and that the peak recovers to baseline after a given purging time. FIG. 21B also shows the time delay resulting from the low flow rates of the syringe pump. Typically a 20 s lag time occurs from the start of the syringe pump to the start of the observed FAIMS signal.

Figure 22:
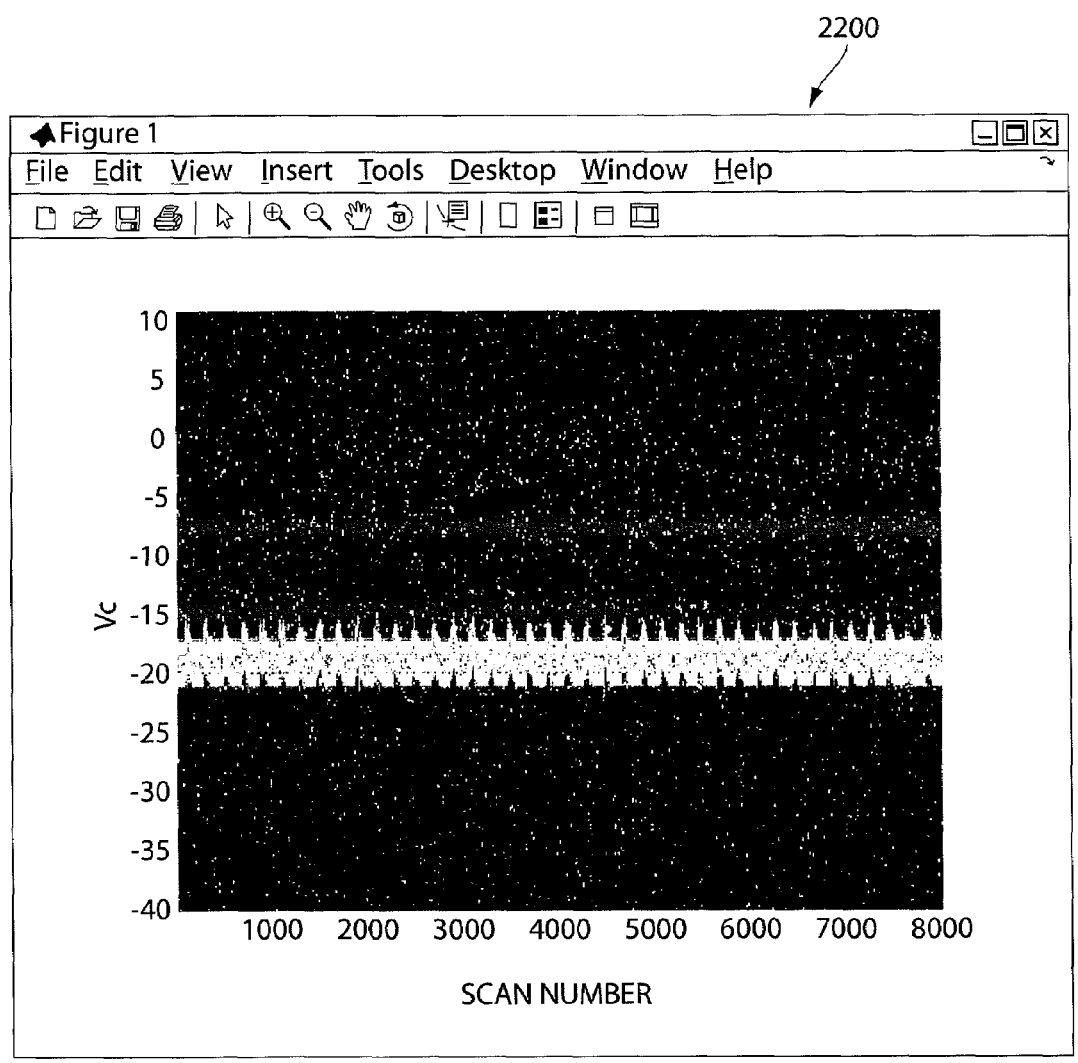
FIG. 22 is a topographical representation of the FAIMS spectra obtained using the ESI/FAIMS system with the interface assembly for a sample of the protein ubiquitin, according to an illustrative embodiment of the invention.

Datasets are typically collected in blocks of 40. A topographical representation 2200 of the FAIMS spectra for one of the 40-replicate blocks of BSA is shown in FIG. 22. The on-off cycles of the sample pump can be clearly seen in the figure as shifts in the main RIP line trace. It is clear that the ESI-FAIMS interface produces a reproducible sample introduction mechanism.

It is contemplated that methods of the invention may be combined with bioinformatic techniques for further data analysis.

Figure 23:
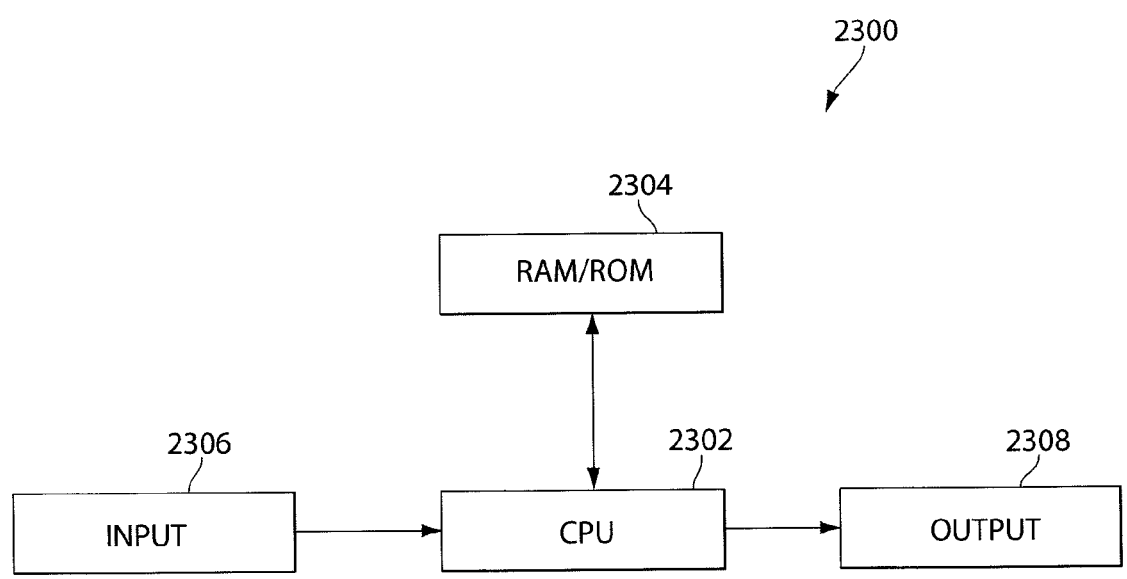
FIG. 23 depicts a computer hardware apparatus suitable for use with the systems and methods described herein, according to an illustrative embodiment of the invention.

FIG. 23 is a schematic 2300 depicting a computer hardware apparatus 2300 suitable for use in any of the methods or systems described herein, or in conjunction with any apparatus described herein. The apparatus 2300 may be a portable computer, a desktop computer, a mainframe, or other suitable computer having the necessary computational speed and accuracy to support the functionality discussed herein. The computer 2300 typically includes one or more central processing units 2302 for executing the instructions contained in the software code which embraces one or more of the methods described herein. Storage 2304, such as random access memory and/or read-only memory, is provided for retaining the code, either temporarily or permanently, as well as other operating software required by the computer 2300. Permanent, non-volatile read/write memory such as hard disks are typically used to store the code, both during its use and idle time, and to store data generated by the software. The software may include one or more modules recorded on machine-readable media such as magnetic disks, magnetic tape, CD-ROM, and semiconductor memory, for example. Preferably, the machine-readable medium is resident within the computer 2300. In alternative embodiments, the machine-readable medium can be connected to the computer 2300 by a communication link. For example, a user of the software may provide input data via the internet, which is processed remotely by the computer 2300, and then output is sent to the user. In alternative embodiments, one can substitute computer instructions in the form of hardwired logic for software, or one can substitute firmware (i.e., computer instructions recorded on devices such as PROMs, EPROMs, EEPROMs, or the like) for software. The term machine-readable instructions as used herein is intended to encompass software, hardwired logic, firmware, object code, and the like.

The computer 2300 is preferably a general purpose computer. The computer 2300 can be, for example, an embedded computer, a personal computer such as a laptop or desktop computer, a server, or another type of computer that is capable of running the software, issuing suitable control commands, and recording information. The computer 2300 includes one or more inputs 2306, such as a keyboard and disk reader for receiving input such as data and instructions from a user, and one or more outputs 2308, such as a monitor or printer for providing results in graphical and other formats. Additionally, communication buses and I/O ports may be provided to link all of the components together and permit communication with other computers and computer networks, as desired.

EQUIVALENTS

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. An interface assembly for delivering an ionized analyte from an ionization apparatus into an ion mobility spectrometer, the interface assembly comprising:
   a capillary tube through which the ionized analyte flows;
   an ion flow generator that draws the ionized analyte from the ionization apparatus into the interface assembly and through the capillary tube; and
   a gas manifold assembly through which a carrier gas flows, the gas manifold assembly disposed in relation to the capillary tube to allow infusion of the ionized analyte into the carrier gas and delivery of the resulting gas stream into the ion mobility spectrometer.

2. The interface assembly of claim 1, wherein the ion flow generator comprises a high voltage assembly that draws the ionized analyte into the interface assembly using a high voltage.

3. The interface assembly of claim 1, wherein the high voltage assembly operates with a potential of up to about 5000 V.

4. The interface assembly of claim 1, wherein the high voltage assembly operates with a potential of about 1000 V or more.

5. The interface assembly of claim 1, wherein the high voltage assembly comprises an electrode plate at a high negative voltage.

6. The interface assembly of claim 1, wherein the high voltage assembly comprises an outer electrode and an inner electrode at different voltages.

7. The interface assembly of claim 1, wherein the ion flow generator comprises an electrical component for drawing the ionized analyte from the ionization apparatus into the interface assembly using an electrical field, a mechanical component for drawing the ionized analyte from the ionization apparatus into the interface assembly using a pressure differential, or both.

8. The interface assembly of claim 1, wherein at least a portion of the gas manifold assembly is disposed about the capillary tube, thereby allowing infusion of the ionized analyte into the carrier gas.

9. The interface assembly of claim 1, wherein the ion flow generator draws a sample gas from the ionization apparatus, the sample gas comprising the ionized analyte.

10. The interface assembly of claim 9, wherein the sample gas further comprises ionized matrix molecules, ionized solvent, or both.

11. The interface assembly of claim 9, wherein non-analyte molecules are filtered from the sample gas in the interface assembly.

12. The interface assembly of claim 9, comprising an orifice through which a break-up gas flows for dissolution of the sample gas.

13. The interface assembly of claim 12, wherein the break-up gas is heated.

14. The interface assembly of claim 12, wherein the break-up gas comprises air or nitrogen.

15. The interface assembly of claim 1, wherein the carrier gas comprises nitrogen.

16. The interface assembly of claim 1, wherein the carrier gas comprises at least one member selected from the group consisting of argon, helium, air, oxygen, and carbon dioxide.

17. The interface assembly of claim 1, wherein at least one of the ionization apparatus and the ion mobility spectrometer operates at about ambient pressure.

18. The interface assembly of claim 1, wherein both the ionization apparatus and the ion mobility spectrometer operate at about ambient pressure.

19. The interface assembly of claim 1, wherein the ionization apparatus is an ambient pressure matrix-assisted laser desorption ionization apparatus or an electrospray ionization apparatus.

20. The interface assembly of claim 1, wherein the ionization apparatus is an ambient pressure matrix-assisted laser desorption ionization apparatus.

21. The interface assembly of claim 1, wherein the ion mobility spectrometer is a field asymmetric ion mobility spectrometer.

22. The interface assembly of claim 1, wherein the ionization apparatus is an ambient pressure matrix-assisted laser desorption ionization apparatus or an electrospray ionization apparatus, and wherein the ion mobility spectrometer is a field asymmetric ion mobility spectrometer.

23. The interface assembly of claim 1, further comprising a mount block comprising a mechanism for detachably connecting the interface assembly to the ionization apparatus.

24. The interface assembly of claim 23, wherein the mechanism is a hinge-and-latch mechanism.

25. The interface assembly of claim 23, wherein the mechanism allows interchange between two or more machines that serve as the ionization apparatus.

26. The interface assembly of claim 23, wherein the mechanism allows interchange between an ambient pressure matrix-assisted laser desorption ionization apparatus and an electrospray ionization apparatus as the ionization apparatus.

* * * * *